(12) United States Patent
Bailey et al.

(10) Patent No.: US 6,369,270 B1
(45) Date of Patent: Apr. 9, 2002

(54) BENZOIC ACID INTERMEDIATES TO 4-BENZOYLISOXAZOLE HERBICIDES

(75) Inventors: Angela Jacqueline Bailey; Michael Gingell; David William Hawkins, all of Ongar (GB)

(73) Assignee: Rhone Poulenc Agriculture Limited, Ongar (GB)

( * ) Notice: Subject to any disclaimer, the term of this patent is extended or adjusted under 35 U.S.C. 154(b) by 0 days.

(21) Appl. No.: 09/420,492

(22) Filed: Oct. 19, 1999

Related U.S. Application Data

(62) Division of application No. 08/858,578, filed on May 19, 1997, now Pat. No. 5,998,653, which is a division of application No. 08/663,048, filed as application No. PCT/EP94/04091 on Dec. 6, 1994, now Pat. No. 5,658,858.

(30) Foreign Application Priority Data

Dec. 15, 1993 (GB) .............................................. 9325618

(51) Int. Cl.[7] ...................... C02C 229/00; C02C 261/00
(52) U.S. Cl. .......................................... 562/456; 560/29
(58) Field of Search ............................. 560/29; 562/456

(56) References Cited

U.S. PATENT DOCUMENTS 5,656,573 A    8/1997   Roberts et al.

FOREIGN PATENT DOCUMENTS

| EP | 0418175 | 3/1991 |
|---|---|---|
| EP | 0487357 | 5/1992 |
| EP | 0527036 | 2/1993 |
| EP | 0527037 | 2/1993 |
| EP | 0560482 | 9/1993 |
| EP | 0560483 | 9/1993 |
| WO | 94/14782 | 7/1994 |

OTHER PUBLICATIONS

Chemical Abstracts, vol. 82, 1975, 57592s.

Primary Examiner—Paul J. Killos
(74) Attorney, Agent, or Firm—Burns, Doane, Swecker & Mathis, L.L.P.

(57) ABSTRACT

Compound of the formula

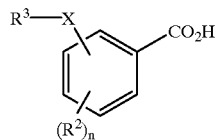

(XVI)

are useful as intermediates to new 4-benzoylisoxazoles.

6 Claims, No Drawings

BENZOIC ACID INTERMEDIATES TO 4-BENZOYLISOXAZOLE HERBICIDES

This application is a divisional of U.S. patent application Ser. No. 08/858,578, filed May 19, 1997 now U.S. Pat. No. 5,998,653, now allowed, which is divisional of U.S. patent application Ser. No. 08/663,048, filed Sep. 6, 1996, now U.S. Pat. No. 5,658,858, which is the U.S. national phase of International Application No. PCT/EP94/04051, filed Dec. 6, 1994. Patent application Ser. No. 08/663,048 is incorporated by reference herein in its entirety and relied upon.

FIELD OF THE INVENTION

This invention relates to novel 4-benzoylisoxazole derivatives, compositions containing them, processes for their preparation, intermediates in their preparation and their use as herbicides.

BACKGROUND ART

Herbicidal 4-benzoylisoxazoles are described in European Patent Publication Numbers 0418175, 0487357, 0527036, 0527037, 0560482, and 0560483.

DESCRIPTION OF THE INVENTION

The present invention provides 4-benzoylisoxazole derivatives of formula (I):

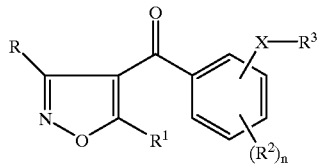

(I)

wherein:

R represents the hydrogen atom or a group —$CO_2R^4$;

$R^1$ represents:

a straight- or branched-chain alkyl group containing up to six halogen atoms; or a cycloalkyl group containing from three to six carbon atoms optionally substituted by one or more $R^5$ groups or one or more halogen atoms;

$R^2$ represents:

a halogen atom;

a straight- or branched-chain alkyl, alkenyl or alkynyl group containing up to six carbon atoms optionally substituted by one or more halogen atoms;

a straight- or branched-chain alkyl group containing up to six carbon atoms which is substituted by one or more groups —$OR^5$; or a group selected from nitro, cyano, —$CO_2R^5$, —$S(O)_pR^{6'}$, —$O(CH_2)_mOR^5$, —$COR^5$, —$NR^5R^6$, —$N(R^8)SO_2R^7$, —$OR^5$, —$OSO_2R^7$, —$(CR^9R^{10})_rSO_qR^7$ and —$CONR^5R^6$;

$R^3$ represents a group —$C(Z)=Y$;

in which Y=O or S (preferably Y represents O);

Z represents a group $R^{63}$, —$NR^{60}R^{61}$, —$N(R^{60})$—$NR^{61}R^{62}$, —$SR^{63}$, —$OR^{63}$; wherein $R^{60}$, $R^{61}$ and $R^{62}$ which may be the same or different each represents:

a hydrogen atom, a straight- or branched-chain alkyl, alkenyl or alkynyl group containing up to six carbon atoms optionally substituted by one or more halogen atoms; or a group —$(CH_2)_w$—[phenyl optionally substituted by one to five groups $R^{21}$];

$R^{63}$ represents:

a straight- or branched-chain alkyl, alkenyl or alkynyl group containing up to six carbon atoms optionally substituted by one or more halogen atoms, or a group —$(CH_2)_w$—[phenyl optionally substituted by one to five groups $R^{21}$];

X represents a group —$N(R^{8'})$—; in which, $R^8$ represents:

the hydrogen atom;

a straight- or branched-chain alkyl, alkenyl or alkynyl group containing up to ten carbon atoms optionally substituted by one or more halogen atoms;

a cycloalkyl group containing from three to six carbon atoms;

—$(CH_2)_w$—[phenyl optionally substituted by from one to five groups $R^{21}$]; or a group —$OR^{11}$;

and the groups $R^3$ and $R^{8'}$ in the grouping of formula —$N(R^{8'})$—$R^3$ may, together with the nitrogen atom to which they are attached, form a 4 to 6 membered ring of formula (AA), (AB), (AC) or (AD):

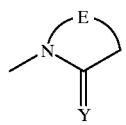

(AA)

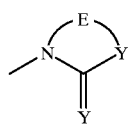

(AB)

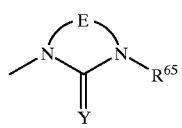

(AC)

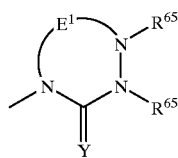

(AD)

wherein

E represents an alkylene or alkylidene chain of 1 or 3 carbon atoms optionally substituted by a group $R^{64}$ and $E^1$ represents alkyl of 1 or 2 carbon atoms optionally substituted by a group $R^{64}$, wherein $R^{64}$ represents an optionally halogenated straight- or branched-chain alkyl group containing up to 6 carbon atoms and $R^{65}$ represents the hydrogen atom or an optionally halogenated straight- or branched-chain alkyl group containing up to 6 carbon atoms; in formula (AB) the groups Y may be the same or different;

n represents zero or an integer from one to four; where n is greater than one the groups $R^2$ may be the same or different;

$R^4$ represents a straight- or branched-chain alkyl group containing up to six carbon atoms optionally substituted by one or more halogen atoms;.

$R^5$ and $R^6$, which may be the same or different, each represents:

the hydrogen atom, a straight- or branched-chain alkyl, alkenyl or alkynyl group containing up to six carbon atoms optionally substituted by one or more halogen atoms;

$R^{6'}$ is as hereinbefore defined for $R^6$ but excluding the hydrogen atom;

$R^7$ represents:

a straight- or branched-chain alkyl, alkenyl or alkynyl group containing up to six carbon atoms optionally substituted by one or more halogen atoms;

a cycloalkyl group containing from three to six carbon atoms;

a group —$(CH_2)_w$—[phenyl optionally substituted by from one to five groups $R^{21}$];

$R^8$ is as hereinbefore defined for $R^{8'}$;

$R^9$ and $R^{10}$ represent a group selected from:

the hydrogen atom;

a straight- or branched-chain alkyl group containing up to six (preferably up to 3) carbon atoms optionally substituted by one or more halogen atoms;

$R^{11}$ represents a straight- or branched-chain alkyl group containing up to six carbon atoms optionally substituted by one or more halogen atoms;

$R^{21}$ represents:

a halogen atom;

a straight- or branched-chain alkyl group containing up to three carbon atoms optionally substituted by one or more halogen atoms;

or a group selected from nitro, cyano, —$S(O)_pR^{5'}$ and —$OR^5$;

wherein $R^{5'}$ is as hereinbefore defined for $R^5$ but excluding the hydrogen atom;

m represents one, two or three;

p represents zero, one or two;

q represents zero, one or two;

t represents one, two, three or four (preferably one); and w represents zero or one;

and agriculturally acceptable salts thereof, which possess valuable herbicidal properties.

Furthermore in certain cases the groups R, $R^1$, $R^2$ and others may give rise to geometric and/or optical isomers. All such forms are embraced by the present invention By the term "agriculturally acceptable salts" is meant salts the cations or anions of which are known and accepted in the art for the formation of salts for agricultural or horticultural use. Preferably the salts are water-soluble.

The compounds of the invention, in some aspects of their activity, for example in their control of important weeds found in cereal crops, e.g. *Galium aparine, Alopecurus myosuroides* and *Avena fatua* (especially *Galium aparine*), and in their selectivity in important cereal crops, e.g. wheat and maize, show advantages over known compounds.

DETAILED DESCRIPTION OF THE INVENTION

The compounds are of particular interest against monocotyledonous weeds by post-emergence application.

Preferably the 2-position of the benzoyl ring is substituted, most preferably by the group —$XR^3$.

Preferably the 5- and 6-positions of the benzoyl ring are unsubstituted.

Preferred compounds of formula (I) are those wherein:

$R^1$ represents:

a straight- or branched-chain alkyl group containing up to six carbon atoms which is optionally substituted by one or more halogen atoms; or a cycloalkyl group containing from three to six carbon atoms optionally substituted by one or more methyl groups or one or more halogen atoms;

$R^2$ represents:

a halogen atom;

a straight- or branched-chain alkyl, alkenyl or alkynyl group containing up to six carbon atoms optionally substituted by one or more halogen atoms;

a straight- or branched-chain alkyl group containing up to six carbon atoms which is substituted by a group —$OR^5$; or a group selected from nitro, cyano, —$CO_2R^5$, —$S(O)_pR^{6'}$, —$O(CH_2)_mOR^5$, —$COR^5$, —$NR^8SO_2R_7$, —$OR^5$, —$CH_2SO_qR^7$;

X represents a group —$N(R^{8'})$—; or the groups $R^3$ and $R^{8'}$ in the grouping of formula —$N(R^{8'})$—$R^3$, together with the nitrogen atom to which they are attached, form a ring of formula (AB) above;

Z represents a group $R^{63}$, —$NR^{60}R^{61}$, —$SR^{63}$ or —$OR^{63}$; and n represents zero, one, two or three.

A further preferred class of compounds of formula (I) are those wherein:

$R^1$ represents:

methyl ethyl i-propyl, cyclopropyl or 1-methylcyclopropyl;

$R^2$ represents:

a halogen atom;

a straight- or branched-chain alkyl or alkenyl group containing up to four carbon atoms optionally substituted by one or more halogen atoms; or a group selected from —$COR^5$, —$CO_2R^5$, —$S(O)_pR^{6'}$, —$CH_2SO_qR^7$, —$O(CH_2)_mOR^5$, —$OR^5$ and —$NR^8SO_2R^7$;

$R^5$ and $R^{6'}$, which may be the same or different, each represents:

a straight- or branched-chain alkyl group containing up to three carbon atoms optionally substituted by one or more halogen atoms;

$R^7$ represents:

a straight- or branched-chain alkyl group containing up to four carbon atoms optionally substituted by one or more halogen atoms;

$R^8$ represents:

the hydrogen atom or a straight- or branched-chain alkyl group containing up to four carbon atoms optionally substituted by one or more halogen atoms;

m represents two or three;

q represents zero, one or two;

n represents zero, one or two;

$R^{8'}$ represents hydrogen or a straight- or branched-chain alkyl group containing up to six carbon atoms optionally substituted by one or more halogen atoms;

Y represents oxygen;

Z represents $R^{63}$ or —$OR^{63}$;

in which $R^{63}$ represents a straight- or branched-chain alkyl group containing up to six carbon atoms optionally substituted by one or more halogen atoms; and —$OR^{63}$ represents a straight- or branched-chain alkoxy, alkenyloxy or alkynyloxy group containing up to six carbon atoms optionally substituted by one or more halogen atoms.

A further preferred class of compounds of formula I are those wherein:

R represents hydrogen or —$CO_2R^4$ wherein $R^4$ is ethyl;

$R^1$ represents:

methyl, ethyl, i-propyl, cyclopropyl, or 1-methylcyclopropyl;

$R^2$ represents:

a halogen atom;

a straight- or branched-chain alkyl group containing up to four carbon atoms optionally substituted by one or more halogen atoms; or a group —$OR^5$ or —$S(O)_pR^{6'}$;

in which $R^5$ and $R^{6'}$, which may be the same or different, each represents:

a straight- or branched-chain alkyl group containing up to three carbon atoms optionally substituted by one or more halogen atoms;

Y represents oxygen;

Z represents:

a group $R^{63}$ or —$OR^{63}$; in which $R^{63}$ represents a straight- or branched-chain alkyl group containing up to six carbon atoms optionally substituted by one or more halogen atoms; and n represents zero, one or two.

A further preferred class of compounds of formula I are those wherein:

R represents hydrogen or —$CO_2Et$;

$R^1$ represents cyclopropyl or isopropyl;

$R^2$ represents halogen, —$OR^5$, —$CF_3$, methyl or —$S(O)_p$Me;

$R^{8'}$ represents a straight- or branched-chain alkyl or alkenyl group containing up to four carbon atoms;

Y represents oxygen;

Z represents $R^{63}$, —$SR^{63}$ or —$OR^{63}$;

$R^{63}$ represents:

a straight- or branched-chain alkyl group containing up to four carbon atoms optionally substituted by one or more halogen atoms;

or phenyl;

$R^5$ represents alkyl containing one or two carbon atoms optionally substituted by one or more halogen atoms;

n represents zero, one or two; and p represents zero, one or two.

A further preferred class of compounds of formula I are those wherein:

R represents hydrogen;

$R^1$ represents cyclopropyl;

$R^2$ represents halogen;

$R^{8'}$ represents a straight- or branched-chain alkyl group of one to four carbon atoms;

Y represents oxygen;

Z represents $R^{63}$ or $R^{63}$;

in which $R^{63}$ represents a straight- or branched-chain alkyl group containing up to four carbon atoms optionally substituted by one or more halogen atoms; and n represents one or two.

Particularly important compounds of formula (I) include the following:

1. 4-[4-chloro-2-(N-methylacetamido)benzoyl]-5-cyclopropylisoxazole;
2. 4-[3,4-dichloro-2-(N-ethyl-N-methoxycarbonylamino) benzoyl]-5-cyclopropylisoxazole;
3. 4-[3,4-dichloro-2-(N-methyl-N-ethoxycarbonylamino) benzoyl]-5-cyclopropylisoxazole;
4. 4-[3,4-dichloro-2-(N-methyl-N-methoxycarbonylamino) benzoyl]-5-cyclopropylisoxazole;
5. 4-[3,4-dichloro-2-(N-methyl-N-isopropyl-oxycarbonylamino)benzoyl]-5-cyclopropylisoxazole;
6. 4-[4-bromo-3-ethoxy-2-(N-ethyl-N-methoxy-carbonylamino)benzoyl]-5-cyclopropylisoxazole;
7. 4-[4-bromo-2-(N-ethyl-N-methoxycarbonylamino)-3-(2,2,2-trifluoroethoxy)benzoyl]-5-cyclopropylisoxazole;
8. 4-[4-bromo-2-(N-ethyl-N-methoxycarbonylamino)-3-methoxybenzoyl]-5-cyclopropylisoxazole;
9. 4-[3,4-dichloro-2-(N-propyl-N-methoxycarbonylamino) benzoyl]-5-cyclopropylisoxazole;
10. 4-(3,4-dichloro-2-(N-isopropyl-N-methoxy-carbonylamino)benzoyl]-5-cyclopropylisoxazole;
11. 4-[3,4-dichloro-2-(N-alkyl-N-methoxycarbonylamino) benzoyl]-5-cyclopropylisoxazole;
12. 4-[3,4-dichloro-2-(N-ethyl-N-ethoxycarbonylamino) benzoyl]-5-cyclopropylisoxazole;
13. 4-[3,4dichloro-2-(N-ethyl-N-propyloxycarbonylamino) benzoyl]-5-cyclopropylisoxazole;
14. 4-[3,4dichloro-2-(N-ethyl-N-isopropyl-oxycarbonylamino)benzoyl]-5-cyclopropylisoxazole;
15. 4-[3,4chloro-2-(N-ethyl-N-n-butyloxycarbonylamino) benzoyl]-5cyclopropylisoxazole;
16. 4-[3,4-dichloro-2-(N-ethyl-N-methoxycarbonylamino) benzoyl]-5-isopropylisoxazole;
17. 4-[4-bromo-3-ethoxy-2-(N-methyl-N-methoxycarbonylamino)benzoyl]-5-cyclopropylisoxazole;
18. 4-[4chloro-2-(N-methyl-N-methoxycarbonylamino) benzoyl]-5-cyclopropylisoxazole;
19. 5-cyclopropyl-4-[3,4-difluoro-2-(N-methyl-N-methoxycarbonylamino)benzoyl]isoxazole;
20. 4-[4-chloro-2-(N-ethyl-N-methoxycarbonylamino) benzoyl]-5-cyclopropylisoxazole;
21. 4-[4-chloro-2-(N-propyl-N-methoxycarbonylamino) benzoyl]-5-cyclopropylisoxazole;
22. 5-cyclopropyl-4-[2-(N-ethyl-N-methoxy-carbonylamino)-4-fluorobenzoyl]isoxazole;
23. 5-cyclopropyl-4-[2-(N-ethyl-N-methoxy-carbonylamino)-4-trifluoromethylbenzoyl]isoxazole;
24. 5-cyclopropyl-4-[2-(N-ethyl-N-ethoxycarbonylamino)-4-trifluoromethylbenzoyl]isoxazole;
25. 5-cyclopropyl-4-[2-(N-ethyl-N-isopropyl-oxycarbonylamino)-4-trifluoromethylbenzoyl]isoxazole;
26. 5-cyclopropyl-4-[2-(N-methyl-N-methoxy-carbonylamino)-4-trifluoromethylbenzoyl]isoxazole;
27. 4-[4-bromo-2-(N-methyl-N-methoxycarbonylamino) benzoyl]-5-cyclopropylisoxazole;
28. 5-cyclopropyl-4-[4-iodo-2-(N-methyl-N-methoxycarbonylamino)benzoyl]isoxazole;
29. 5-cyclopropyl-4-[2-(N-methyl-N-methoxy-carbonylamino)-4-trifluoromethoxybenzoyl]isoxazole;
30. 4-[4-chloro-2-(N-isobutyl-N-methoxycarbonylamino) benzoyl]-5-cyclopropylisoxazole, 31. 4-[3,4-dichloro-2-(N-methyl-N-methyl-thiocarbonylamino)benzoyl]-5-cyclopropylisoxazole;
32. 5-cyclopropyl-4-[4-methyl-2-(N-methyl-N-methoxycarbonylamino)benzoyl]isoxazole;
33. 5-cyclopropyl-4-[2-(N-ethyl-N-methoxycarbonylamino)-4-methylsulphonylbenzoyl]isoxazole;
34. 5-cyclopropyl-4-[2-(N-ethyl-N-methoxycarbonylamino)benzoyl]isoxazole;
35. 4-[3-chloro-2-(N-ethyl-N-methoxycarbonylamino)-4-(methylthio)benzoyl]-5-cyclopropylisoxazole;
36. 5-cyclopropyl-4-[2-(N-ethyl-N-methoxycarbonylamino)-3,4-difluorobenzoyl]isoxazole;
37. 5-cyclopropyl-4-[2-(N-ethyl-N-methoxycarbonylamino)-3-fluoro-4-(methylthio)benzoyl]isoxazole;
38. 4-[4-chloro-2-(N-ethyl-N-methoxycarbonylamino)-3-fluorobenzoyl]-5-cyclopropylisoxazole;
39. 4-[3,4-dibromo-2-(N-ethyl-N-methoxycarbonylamino)benzoyl]-5cyclopropylisoxazole;
40. 4-[3-chloro-2-(N-ethyl-N-methoxycarbonylamino)benzoyl]-5-cyclopropylisoxazole;
41. 5-cyclopropyl-4-[2-(N-ethyl-N-phenoxycarbonylamino)-4-trifluoromethylbenzoyl]isoxazole;
42. 4-[4-chloro-2-(N-ethyl-N-ethoxycarbonylamino)benzoyl]-5-cyclopropylisoxazole;
43. 4-[4-chloro-2-(N-propyl-N-propyloxycarbonylamino)benzoyl]-5-cyclopropylisoxazole;
44. 4-[4-chloro-2-(N-propyl-N-ethoxycarbonylamino)benzoyl]-5-cyclopropylisoxazole;
45. 4-[4-chloro-2-(N-propyl-N-n-butyloxycarbonylamino)benzoyl]-5-cyclopropylisoxazole;
46. ethyl 4-[3,4-dichloro-2-(N-methyl-N-methoxycarbonylamino)benzoyl]-5-cyclopropylisoxazole-3-carboxylate;
47. ethyl 4-[3,4-dichloro-2-(N-ethyl-N-methoxycarbonylamino)benzoyl]-5-cyclopropylisoxazole-3-carboxylate;
48. 4-[3-chloro-2-(N-ethyl-N-methoxycarbonylamino)-4-methylsulphonylbenzoyl]-5-cyclopropylisoxazole;
49. 5-cyclopropyl-4-[2-(N-ethyl-N-methoxycarbonylamino)-3-fluoro-4-methylsulphonylbenzoyl]isoxazole; and
50. 5-cyclopropyl-4-[2-(N-ethyl-N-methoxycarbonylamino)-3-fluoro-4-methylsulphinylbenzoyl]isoxazole.

The numbers 1 to 50 are assigned to these compounds for reference and identification hereinafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) in which R represents hydrogen may be prepared by the reaction of a compound of formula (II):

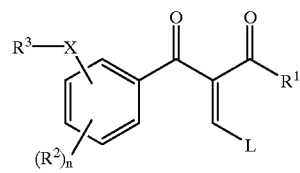

(II)

wherein L is a leaving group and $R^1$, $R^2$, $R^3$, n and X are as hereinbefore defined with hydroxylamine or a salt of hydroxylamine. Hydroxylamine hydrochloride is generally preferred. Generally L is alkoxy, for example ethoxy, or N,N-dialkylamino, for example dimethylamino. The reaction is generally carried out in an organic solvent such as ethanol or acetonitrile or a mixture of a water-miscible organic solvent and water, preferably in a ratio of organic solvent: water of from 1:99 to 99:1, optionally in the presence of a base or acid acceptor such as triethylamine or sodium acetate at a temperature from room temperature to the boiling point of the solvent. The intermediates of formula (II) are novel and as such constitute a further feature of the present invention.

According to a further feature of the present invention compounds of formula (I) in which R represents hydrogen may be prepared by the reaction of a compound of formula (III):

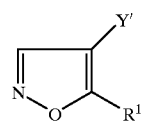

(III)

wherein $R^1$ is as hereinbefore defined and Y' represents a carboxy group or a reactive derivative thereof (such as a carboxylic acid chloride or carboxylic ester), or a cyano group, with an appropriate organometalic reagent such as a Grignard reagent or an organolithium reagent. The reaction is generally carried out in an inert solvent such as ether or tetrahydrofuran at a temperature from 0° C. to the reflux temperature of the mixture.

According to a further feature of the present invention compounds of formula (I) wherein R represents a group —$CO_2R^4$ may be prepared by the reaction of a compound of formula (IV)

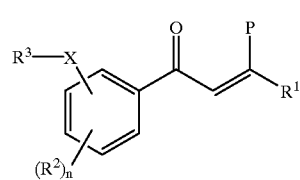

(IV)

wherein $R^1$, $R^2$; $R^3$, X and n are as hereinbefore defined and P is a leaving group such as N,N-dialkylamino, with a compound of formula $R^4O_2CC(Z')$=NOH wherein $R^4$ is as hereinbefore defined and Z' is a halogen atom. Generally Z' is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula I in which R represents a group —$CO_2R^4$ may be prepared by the reaction of a compound of formula (V):

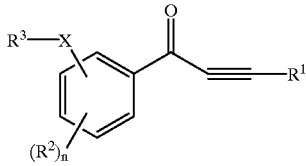

(V)

wherein $R^1$, $R^2$, $R^3$, X and n are as hereinbefore defined with a compound of formula $R^4O_2CC(Z')$=NOH wherein Z' and $R^4$ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula (I) wherein R represents —$CO_2R^4$ may be prepared by the reaction of a salt of compounds of formula (VI):

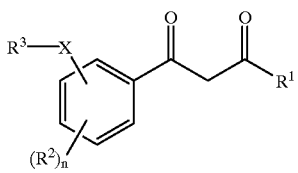

(VI)

wherein $R^1$, $R^2$, $R^3$, X and n are as hereinbefore defined with a compound of formula $R^4O_2CC(Z')$=NOH wherein $R^4$ and Z' are as hereinbefore defined. Preferred salts include sodium or magnesium salts. The reaction may be performed in an inert solvent such as dichloromethane or acetonitrile at a temperature between room temperature and the reflux temperature of the mixture. The salt of a compound of formula (VI) is generally prepared in situ by treating the compound of formula (VI) with a base. Examples of suitable bases include alkaline earth metal alkoxides such as magnesium methoxide.

According to a further feature of the present invention compounds of formula (I) in which X represents —NH— may be prepared by the deprotection of a compound of formula (VII):

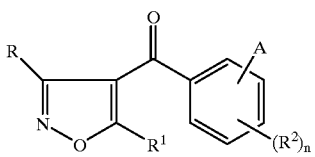

(VII)

wherein R, $R^1$, $R^2$ and n are as hereinbefore defined and A represents —$NX^1R^3$ wherein $R^3$ is as hereinbefore defined and $X^1$ represents a protecting group which can be removed under acidic or neutral reaction conditions.

The protecting group may be for example a benzyl group (which may be removed by hydrogenolysis) or a t-butyloxycarbonyl group (t-BOC). Suitable methods of protection and deprotection are described in the literature (for example in "Protective Groups in Organic Synthesis", by T. W. Greene and P. G. M. Wuts). The intermediates of formula (VII) are novel and as such constitute a further feature of the present invention.

According to a further feature of the present invention compounds of formula (I) in which $R^3$ represents a group —C(Z)=Y and Z is selected from $R^{63}$, —$NR^{60}R^{61}$ (wherein $R^{60}$ and $R^{61}$ are not hydrogen), —$SR^{63}$ or —$OR^{63}$ may be prepared by the reaction of a compound of formula (VIII):

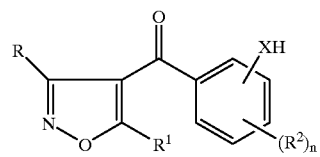

(VIII)

with a compound of formula $A^1$—CZ(=Y), wherein $A^1$ is a leaving group and Z is as defined above. Preferably $A^1$ is chlorine. The reaction is generally performed in the presence of a weak base, e.g. caesium carbonate and in an inert solvent (e.g. acetonitrile) at a temperature from room temperature to reflux.

According to a further feature of the present invention compounds of formula (I) in which $R^3$ represents a group —C(Z)=Y and Z is —$NHR^{60}$ may be prepared by the reaction of the corresponding compound of formula (VII) with a compound of formula $R^{60}$—N=C=Y, wherein $R^{60}$ is as hereinbefore defined. The reaction is generally performed in an inert solvent at a temperature from room temperature to reflux.

Intermediates in the preparation of compounds of formula (I) may be prepared by the application or adaptation of known methods.

Compounds of formula (II) may be prepared by the reaction of compounds of formula (VI) with either a trialkyl orthoformate such as triethyl orthoformate or a dimethylformamide dialkyl acetal such as dimethylformamide dimethyl acetal The reaction with a trialkyl orthoformate can be carried out in the presence of acetic anhydride at the reflux temperature of the mixture and the reaction with dialkylformamide dialkyl acetal is carried out optionally in the presence of an inert solvent at a temperature from room temperature to the reflux temperature of the mixture.

Compounds of formula (IV) may be prepared by the reaction of a compound of formula $R^1C(P)$=$CH_2$ with a benzoyl chloride of formula (IX):

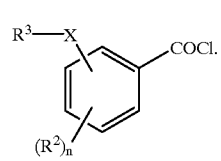

(IX)

The reaction is generally carried out in the presence of an organic base such as triethylamine in an inert solvent such as toluene or dichloromethane at a temperature between −20° C. and room temperature.

Compounds of formula (V) may be prepared by the metallation of the appropriate acetylene of formula (X):

   (X)

followed by reaction of the metal salt thus obtained with a benzoyl chloride of formula (IX). The metallation is generally performed using n-butyl lithium in an inert solvent such as ether or tetrahydrofuran at a temperature from −78° C. to 0° C. The subsequent reaction with the benzoyl chloride is carried out between −78° C. and room temperature.

Compounds of formula (VI) may be prepared by the reaction of an acid chloride of formula (IX) with the metal salt of a compound of formula (XI):

   (XI)

wherein $R^1$ is as hereinbefore defined, to give a compound of formula (XI):

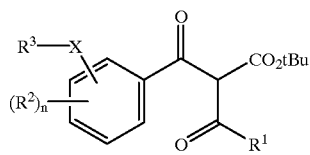   (XII)

wherein $R^1$, $R^2$ $R^3$, X and a are as hereinbefore defined, which is subsequently decarboxylated to give a compound of formula (VI). Generally the reaction to produce the compound of formula (XII) is performed in a solvent such as a lower alcohol, preferably methanol, in the presence of a metal preferably magnesium. The reaction may also be performed using a pre-prepared metal salt of a compound of formula (XI). The decarboxylation is generally performed by refluxing the compound of formula (XII) in the presence of a catalyst, such as paratoluenesulphonic acid or trifluoroacetic acid, in an inert solvent e.g. toluene or 1,2-dichloroethane.

Compounds of formula (VI) may also be prepared by the reaction of a benzoic acid ester of formula (XV):

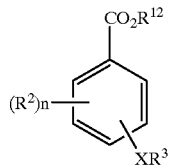   (XIII)

wherein $R^2$, $R^3$, X and n are as hereinbefore defined and $R^{12}$ represents a lower alkyl group, with a compound of formula (XIV):

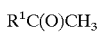   (XIV)

wherein $R^1$ is as hereinbefore defined. The reaction is generally performed in a solvent such as ether, tetrahydrofuran or N,N-dimethylformamide, in the presence of a base, preferably an alkali metal base such as sodium hydride, at a temperature from 0° C. to the reflux temperature.

Compounds of formula (VI) in which —$XR^3$ represents —$NHCONR^{60}R^{61}$ may also be prepared by the reaction of a compound of formula (XV):

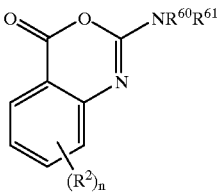   (XV)

with a ketone of formula (XIV) above in the presence of a base, preferably lithium diisopropylamide in an inert solvent at a temperature from 78° C. to room temperature.

Compounds of formula (VII) may be prepared by the processes hereinbefore described for preparing compounds of formula (I) in which R, $R^1$, $R^2$ and n are as hereinbefore defined and the group —$XR^3$ is replaced by the group A.

Compounds of formula (VIII) may be prepared by the hydrolysis of the corresponding compound of formula (I) in which $R^3$ is replaced by a protecting group, for example alkylsulphonyl (preferably methylsulphonyl). The hydrolysis is generally performed using an acid, preferably sulphuric acid, in an inert solvent (e.g. acetic acid) at a temperature from room temperature to reflux. Compounds of formula (I) in which $R^3$ is replaced by a protecting group may be prepared by the processes hereinbefore described for preparing compounds of formula (I) in which R, $R^1$, $R^2$ and n are as hereinbefore defined and the group $R^3$ is replaced by a protecting group.

Acid chlorides of formula (IX) may be prepared by the reaction of a benzoic acid of formula (XVI):

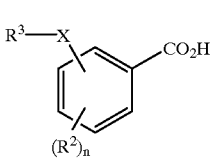   (XVI)

with a chlorinating agent, for example thionyl chloride at the reflux temperature of the mixture. In some cases the benzoyl chlorides may also be prepared by reaction of the benzoic acid with oxalyl chloride in a solvent such as 1,2-dichloroethane at from ambient to reflux temperature.

A number of the benzoic acids of formula (XVI) are novel and as such constitute a flirter feature of the present invention. Compounds of formula (XVI) in which $R^2$ represents a halogen atom or a group selected from trifluoromethyl, methyl, $C_{1-2}$ haloalkoxy and $S(O)_p$Me wherein p is zero, one or two; X represents —$NR^{8'}$ wherein $R^8$ represents alkyl or alkenyl containing up to four carbon atoms optionally substituted by one or more halogen atoms; n represents one or two; $R^3$ represents —C(Z)=Y wherein Y is oxygen, Z is $R^{63}$ or —$OR^{63}$ and $R^{63}$ represents alkyl containing up to four carbon atoms optionally substituted by one or more halogen atoms, are especially preferred.

Compounds of formula (XV) may be prepared by the application or adaptation of known methods, for example as described in Acta. Chim. Acad. Sci. 107(1), 57 (1981).

Compounds of formula (XVI) in which the group —XR³ is ortho to the acid group and R³ is —C(O)R⁶³ may be prepared by the reaction of a compound of formula (XVII):

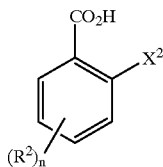

(XVII)

wherein X² is chlorine or preferably bromine or iodine, with a compound of formula R⁸'NHC(O)R⁶³ in the presence of a strong base. Generally the reaction is performed in the presence of a catalyst e.g. copper (I) chloride or preferably copper (I) bromide or iodide, in an inert solvent such as dioxan or toluene. The preferred strong base is sodium hydride and the reaction is conveniently performed at a temperature from 50° C. to reflux Intermediates of formula (VI) in which the group —XR³ is ortho to the carbonyl group and represents a group R⁸'NC(O)R⁶³ may be prepared by the reaction of a compound of formula (XVIII):

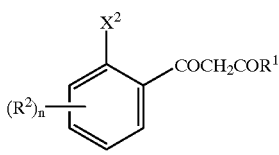

(XVIII)

wherein X² is chlorine or preferably bromine or iodine, with a compound of formula R⁸'NHC(O)R⁶³ in the presence of a strong base. Generally the reaction is performed in the presence of a catalyst e.g. copper (I) chloride or preferably copper (I) bromide or iodide, in an inert solvent such as dioxan or toluene. The preferred strong base is sodium hydride and the reaction is conveniently performed at a temperature from 50° C. to reflux.

Intermediates of formula (XVI) in which R³ represents —CO₂R⁶³ may be prepared by the reaction of the corresponding compound of formula (XVI) in which R³ represents hydrogen with a compound of formula Cl—CO₂R⁶³ in the presence of a base. The base may be pyridine or triethylamine or preferably an alkali metal carbonate e.g. sodium carbonate and the reaction is performed in an inert solvent (e.g. water) at a temperature from 0° C. to 100° C., for example according to the method described in Org. Synthesis Coll. Vol. 3, 167.

Intermediates of formula (M), (X), (XI), (XIII), (XIV), (XVII) and (XVM) are known or may be prepared by the application or adaptation of known methods.

Agriculturally acceptable salts of compounds of formula (I) may be prepared by the application or adaptation of known methods.

Those skilled in the art will appreciate that some compounds of formula (I) may be prepared by the interconversion of other compounds of formula (I) and such interconversions constitute yet more features of the present invention. Examples of such interconversions are hereafter described.

According to a further feature of the present invention compounds in which p and/or q is one or two may be prepared by the oxidation of the sulphur atom(s) of the corresponding compounds in which p and/or q is 0 or 1. The oxidation of the sulphur atom(s) is generally carried out using for example 3-chloroperoxybenzoic acid in an inert solvent such as dichloromethane at a temperature from −40° C. to room temperature.

The following examples illustrate the preparation of compounds of formula (I) and the following reference examples illustrate the preparation of intermediates of the invention. In the present specification b.p. means boiling point; m.p. means melting point; cPr represents cyclopropyl. Where the letters NMR appear, the characteristics of the proton nuclear magnetic resonance spectrum follow (in ppm, solvent CDCl₃ unless otherwise stated).

EXAMPLE 1

Hydroxylamine hydrochloride (0.1 g) was added to a stirred solution of 1-[4-chloro-2-(N-methylacetamido)phenyl]-3-cyclopropyl-2-dimethylaminomethylenepropane-1,3-one (0.32 g) in ethanol. The mixture was stirred for 0.75 hours and evaporated to dryness. Water was added to the residue, which was extracted (dichloromethane). The extract was dried (magnesium sulphate) and evaporated to give an oil. This was purified by chromatography eluting with ethyl acetate/dichloromethane (1:8) to give 4-[4-chloro-2-(N-methylacetamido)benzoyl]-5-cyclopropylisoxazole, (compound number 1, 0.12 g), m.p. 106.5–107.5° C., as a white solid.

EXAMPLE 2

Hydroxylamine hydrochloride (0.53 g) and sodium acetate (0.63 g) were added to a stirred solution of 1-[3,4-dichloro-2-(N-ethyl-N-methoxycarbonylamino)phenyl]-3-cyclopropyl-2-ethoxymethylenepropane-1,3-dione (2.88 g) in ethanol. After 05 hours water was added, and the mixture extracted (dichloromethane), dried (magnesium sulphate) and evaporated to dryness. Purification by chromatography gave 4-[3,4-dichloro-2-(N-ethyl-N-methoxycarbonylamino)benzoyl]-5-cyclopropylisoxazole (compound number 2, 1.09 g), m.p. 76–78° C. as a white solid.

By proceeding in a similar manner the following compounds of the invention were prepared from the appropriately substituted starting materials:

4-[3,4-chloro-2-(N-methyl-N-ethoxycarbonylamino)benzoyl]-5-cyclopropylisoxazole, (compound number 3), m.p. 124.5–127.5° C.

4-[3,4-dichloro-2-(N-methyl-N-methoxycarbonylamino)benzoyl]-5-cyclopropylisoxazole (compound number 4). m.p. 129–131° C.

4-[3,4-dichloro-2-(N-methyl-N-isopropyloxycarbonylamino)benzoyl]-5-cyclopropylisoxazole (compound number 5), NMR 0.95(d, 3H), 1.1(d,3H), 1.3(m,2H), 1.4(m,2H), 2.8(m,1H), 3.2(s, 3H), 4.85(m,1H), 7.3(d,1H), 7.55(d,1H), 8.1(s,1H).

4-[4-bromo-3-ethoxy-2-(N-ethyl-N-methoxycarbonylamino)benzoyl]-5-cyclopropylisoxazole (compound number 6), NMR 1.3(m,10H), 2.75(m,1H), 3.45 (s, 3H), 3.7(m,3H), 4.0(m,2H), 7.05(d,1H), 7.6(d,1H), 8.15 (s,1H).

4-[4-bromo-2-(N-ethyl-N-methoxycarbonylamino)-3-(2,2,2-trifluoroethoxy)benzoyl]-5-cyclopropylisoxazole (compound number 7), NMR 1.2(m,10H), 2.7(m,1H), 3(s, 3H), 3.65(m,2H), 4.2(m,1H), 4.5(m,1H), 7.1(d,1H),7.6(d, 1H), 8.1(s,1H).

4-[4-bromo-2-(N-ethyl-N-methoxycarbonylamino)-3-methoxybenzoyl]-5-cyclopropylisoxazole (compound number 8), NMR 1.2(m,6H), 1.4(s,3H), 3.5(s,2H), 3.65(m,3H), 3.85(s,3H), 7.1(d,1H), 7.6(d,1H), 8.0(s,1H).

4-[3,4-dichloro-2-N-propyl-N-methoxycarbonylamino) benzoyl]-5-cyclopropylisoxazole (compound number 9), NMR 0.85(t,3H), 1.6(m,2H), 2.75(m,1H), 3.35(m,2H), 3.6 (s,3H), 7.25(d,1H), 7.55(d,1H), 8.05(s,1H).

4-[3,4-dichloro-2-(N-isopropyl-N-methoxycarbonylamino)benzoyl]-5-cyclopropylisoxazole (compound number 10), NMR 1.1(d,3H), 1.2(d,3H), 1.3(m, 4H), 2.8(m,1H), 3.6(s,3H), 4.3(m,1H), 7.25(d,1H), 7.55(d, 1H), 8.1(s,1H).

4-[3,4-dichloro-2-(N-alkyl-N-methoxycarbonylamino) benzoyl]-5-cyclopropylisoxazole (compound number 11), NMR 1.25(m,2H), 1.35(m,2H), 2.7(m,1H), 3.6(s,3H), 4.15 (m2), 5.0(m,2H), 5.9(m,1H), 7.25(d,1H), 7.55(d,1H), 8.05 (s,1H).

4-[3,4-dichloro-2-(N-ethyl-N-ethoxycarbonylamino) benzoyl]-5-cyclopropylisoxazole (compound number 12), m.p. 98° C.

4-[3,4-dichloro-2-(N-ethyl-N-propyloxycarbonylamino) benzoyl]-5-cyclopropylisoxazole, (compound number 13), m.p. 81–81.5° C.

4-[3,4-dichloro-2-(N-ethyl-N-isopropyloxycarbonylamino)benzoyl]-5-cyclopropylisoxazole (compound number 14), m.p. 78° C.

4-[3,4-dichloro-2-(N-ethyl-N-n-butyloxycarbonylamino]-5-cyclopropylisoxazole (compound number 15), NMR 0.85(t,3H), 1.1–1.6(m,11H), 2.8(m,1H), 3.47(m,1H), 3.7(m,1H), 3.9(m,1H), 4.1(m,1H), 7.3(d,1H), 7.56(d,1H), 8.07(s,1H).

4-[3,4-dichloro-2-(N-ethyl-N-methoxycarbonylamino) benzoyl]-5-isopropylisoxazole (compound number 16), m.p. 90–91° C.

EXAMPLE 3

A mixture of 4-[4-bromo-3-ethoxy-2-(methylamino, benzoyl]-5-cyclopropylisoxazole (0.096 g), methyl chloroformate (0.08 ml) and caesium carbonate (0.04 g) in acetonitrile was heated under reflux for 3 hours. Dichloromethane and water were added to the cooled mixture, the organic phase separated, dried (anhydrous magnesium sulphate) and evaporated in vacuo to give, after purification, 4-[4-bromo-3-ethoxy-2-(N-methyl-N-methoxycarbonylamino)benzoyl]-5-cyclopropylisoxazole (compound number 17, 0.07 g) as a yellow gum, NMR 1.25(m,2H), 1.35(m,2H), 1.46(t,3H), 2.7(m,1H), 3.25(s,3H), 3.45(s,3H), 4.0(m,2H), 7.1(d,1H), 7.6(d,1H), 8.2(s, 1H).

By proceeding in a similar manner the following compounds of the invention were prepared from the appropriately substituted starting materials:

4-[4-chloro-2-(N-methyl-N-methoxycarbonylamino) benzoyl]-5-cyclopropylisoxazole (compound number 18), NMR 1.2(m,2H), 1.3(m,2H), 2.7(m,1H), 3.2(s,3H), 3.5(brs, 3H), 7.4(m,3H), 8.2(s,1H).

5-cyclopropyl-4-[3,4-difluoro-2-N-methyl-N-methoxycarbonylamino)benzoyl]isoxazole (compound number 19) as a white solid, m.p. 118–1195° C.

4-[4-chloro-2-(N-ethyl-N-methoxycarbonylamino) benzoyl]-5-cyclopropylisoxazole (compound number 20), NMR 1.2(m,7H), 2.7(m,1H), 3.6(m,4H), 7.3(s,1H), 7.4(s, 2H), 8.2(s,1H).

4-[4-chloro-2-(N-propyl-N-methoxycarbonylamino) benzoyl]-5-cyclopropylisoxazole (compound number 21) as a brown oil, NMR 0.8(t,3H), 1.2(m,2H), 1.3(m,2H), 1.6(q, 2H), 2.6(m,1H), 3.5(m,5H), 7.2(s,1H), 7.3(s,2H), 8.1(s,1H).

5-cyclopropyl-4-[2-(N-ethyl-N-methoxycarbonylamino)-4-fluorobenzoyl]isoxazole (compound number 22), NMR 1.2(m,7H), 1.6(m,1H), 3.5(m,4H), 6.95(m,2H), 7.4(t,1H), 8.1(s,1H).

5-cyclopropyl-4-[2-(N-ethyl-N-methoxycarbonylamino)-4-trifluoromethylbenzoyl]isoxazole (compound number 23), m.p. 81.7–83.7° C.

5-cyclopropyl-4-[2-(N-ethyl-N-ethoxycarbonylamino)-4-trifluoromethylbenzoyl]isoxazole (compound number 24), m.p. 89–91.5° C.

5-cyclopropyl-4-[2-(N-ethyl-N-isopropyloxycarbonylamino)-4-trifluoromethylbenzoyl] isoxazole (compound number 25), m.p. 74–76° C.

5-cyclopropyl-4-[2-(N-methyl-N-methoxycarbonylamino)-4-trifluoromethylbenzoyl] isoxazole (compound number 26), NMR 1.2(brs,2H), 1.3 (brs,2H), 2.6(brs,1H), 3.2(s,3H), 3.5(brd,3H), 7.5(m,3H), 8.1(brd,1H).

4-[4-bromo-2-(N-methyl-N-methoxycarbonylamino) benzoyl]-5-cyclopropylisoxazole (compound number 27), NMR 12(brs,2H), 1.3(brs,2H), 2.6(m,1H), 3.2(s,3H), 3.5 (brd,3H), 7.3(d,1H), 7.5(m,2H), 8.1(brd,1H).

5-cyclopropyl-4-[4-iodo-2-(N-methyl-N-methoxycarbonylamino)benzoyl]isoxazole (compound number 28), NMR 1.2(brs,2H), 1.3(brs,2H), 2.6(m,1H), 3.2(s,3H), 35(brd,3H), 7.1(d,1H), 7.6(m,2H), 8.1(brd,1H).

5-cyclopropyl-4-[2-(N-methyl-N-methoxycarbonylamino)-4-trifluoromethoxybenzoyl] isoxazole (compound number 29), NMR 1.1(brs,2H), 1.2 (brs,2H), 2.6(brs,1H), 3.2(s,3H), 3.5(brd,3H), 7.1(r,7.4(d, 1H), 8.1(brd,1H).

4-[4-chloro-2-(N-isobutyl-N-methoxycarbonylamino) benzoyl]-5cyclopropylisoxazole (compound number 30), NMR 0.8(d,6H), 1.2(brs,2H), 1.3(brs,2H), 1.8(m,1H), 2.6 (m,1H), 3.5(m,5H), 7.3(m,3H), 8.1(brs,1H).

4-[3,4-dichloro-2-(N-methyl-N-methylthiocarbonylamino)benzoyl]-5-cyclopropylisoxazole (compound number 31) as a white solid, m.p. 175–177° C.

5-cyclopropyl-4-[4-methyl-2-N-methyl-N-methoxycarbonylamino)benzoyl]isoxazole (compound number 32), NMR 1.2(brs,2H), 1.3(brs,2H), 2.4(s,3H), 2.6 (m,1H), 3.2(s,3H), 3.5(brd,3H), 7.1(m,2H), 7.3(d,1H), 8.1 (brd,1H).

5-cyclopropyl-4-[2-(N-ethyl-N-methoxycarbonylamino)-4-methylsulphonylbenzoyl]isoxazole (compound number 33), NMR 1.2(m,5H), 1.3(m,2H), 2.6(m,1H), 3.1(s,3H), 3.6(brd,5H), 7.6(d,1H). 7.9(m,2H), 8.1(brs,1H).

5-cyclopropyl-4-[2-(N-ethyl-N-methoxycarbonylamino] isoxazole (compound number 34), m.p. 60.5–61.5° C.

4-[3-chloro-2-(N-ethyl-N-methoxycarbonylamino)-4-(methylthio)benzoyl]-5-cyclopropylisoxazole (compound number 35), m.p. 126.5–129° C.

5-cyclopropyl-4-[2-(N-ethyl-N-methoxycarbonylamino)-3,4-difluorobenzoyl]isoxazole (compound number 36), NMR 1.15(m,2H), 1.25(t,3H), 1.35(m,2H), 2.7(m,1H), 3.4 (q,2H), 3.55(s,3H), 7.2(m,2H), 8.1(s,1H).

5-cyclopropyl-4-[2-(N-ethyl-N-methoxycarbonylamino)-3-fluoro-4-(methylthio)benzoyl]isoxazole (compound number 37), NMR 1.15(m,2H), 1.25(m,3H), 1.35(m,2H), 2.55 (s,3H), 2.7(m,1H), 3.4(q,2H), 3.55(s,3H), 7.2(m,2H), 8.15 (s,1H).

4-[chloro-2-(N-ethyl-N-methoxycarbonylamino)-3-fluorobenzoyl]-5-cyclopropylisoxazole (compound number 38), m.p. 103–105° C.

4-[3,4-dibromo-2-(N-ethyl-N-methoxycarbonylamino) benzoyl]-5-cyclopropylisoxazole (compound number 39), NMR 1.15(t,3H), 1.3(m,4H), 2.7(m,1H), 3.6(m,2H), 3.62(s, 3H), 5.3(s,1H), 7.25(d,1H), 7.7(d,1H), 8.1(s,1H).

4-[3-chloro-2-(N-ethyl-N-methoxycarbonylamino) benzoyl]-5-cyclopropylisoxazole (compound number 40), m.p. 88–89° C.

5-cyclopropyl-4-[2-(N-ethyl-N-phenoxycarbonylamino)-4-trifluoromethylbenzoyl]isoxazole (compound number 41), NMR 1.3(m,7H), 2.7(m,1H), 3.8(brd,2H), 6.9(m,1H), 7.2 (m,4H), 7.7(m,3H), 8.1(brd,1H).

4-[4-chloro-2-(N-ethyl-N-ethoxycarbonylamino) benzoyl]-5-cyclopropylisoxazole (compound number 42), NMR 1.15(m,8H), 1.27(m,2H), 2.64(m,1H), 3.6(brs,2H), 3.97(q,2H), 7.3(m,3H), 8.14(s,1H).

4-[4-chloro-2-(N-propyl-N-propyloxycarbonylamino) benzoyl]-5-cyclopropylisoxazole (compound number 43), NMR 0.75(t,3H), 0.82(t,3H), 1.12(m,2H), 1.25(m,2H), 1.46 (m,2H), 157(m,2H), 2.62(m,1H), 3.45(brs,2H), 3.88(t,2H), 72(m,3H), 8.08(s,1H).

4-[4-chloro-2-(N-propyl-N-ethoxycarbonylamino) benzoyl]-5-cyclopropylisoxazole (compound number 44), NMR 0.91(t,3H), 1.12(t,3H), 1.22(m,2H), 1.34(m,2H), 1.65 (m,2H), 2.68(m,1H), 3.54(brs,2H), 4.05(q,2H), 7.3(m,3H), 8.17(s,1H).

4-[4-chloro-2-(N-propyl-N-n-butyloxycarbonylamino) benzoyl]-5-cyclopropylisoxazole (compound number 45), NMR 1.0(m,6H), 1.31(m,2H), 1.38(m,2H), 1.45(m,2H), 1.6 (m,2H), 1.75(m,2H), 2.8(m,1H), 3.62(brs,2H), 4.11(t,2H), 7.4(m,3H), 8.29(s,1H).

EXAMPLE 4

Magnesium turning (0.1 g) were heated under reflux in methanol until dissolved, and a solution of 1-[3,4-dichloro-2-(N-methyl-N-methoxycarbonylamino)phenyl]-3-cyclopropylpropan-1,3-dione (1.3 g) in methanol was added at room temperature. Heating under reflux was resumed for 1 hour, the solvent evaporated and the residue was dissolved in dichloromethane. A solution of ethyl chloroximidoacetate (0.68 g) in dichloromethane was added and the mixture stirred overnight. Hydrochloric acid solution (2M) was added, and the organic layer was extracted, washed (water), dried (anhydrous magnesium sulphate) and the solvent evaporated to give, after recrystailisation from ethanol, ethyl 4-[3,4-dichloro-2-(N-methyl-N-methoxycarbonylamino) benzoyl]-5-cyclopropylisoxazole-3-carboxylate (compound 46, 0.54 g) as white crystals, m.p. 119–122° C.

By proceeding in a similar manner ethyl 4-[3,4-dichloro-2-(N-ethyl-N-methoxycarbonylamino)benzoyl]-5-cyclopropylisoxazole-3-carboxylate (compound 47) was prepared from the appropriately substituted starting materials, NMR 1.1(t,3H), 1.25(m,7H), 2.35(m,1H), 33–3.85(m,2H), 3.6(s,3H), 4.2(m,2H), 7.4(d,1H), 7.52(d, 1H).

EXAMPLE 5 m-Chloroperbenzoic acid (1.81 g of a 50% oil dispersion) was added to a stirred solution of 4-[3-chloro-2-(N-ethyl-N-methoxycarbonylamino)-4-(methylthio)benzoyl]-5-cyclopropyl-isoxazole (compound 35, 0.92 g) in dichloromethane. After 5 hours, a solution of sodium metabisulphite was added and the mixture stirred for 5 minutes. The organic phase was washed with sodium bicarbonate solution and water, dried (anhydrous magnesium sulphate) and evaporated. The residue was triturated (with a hexane/ether solution) to yield 4-[3-chloro-2-(N-ethyl-N-methoxycarbonylamino)-4-methylsulphonylbenzoyl]-5-cyclopropylisoxazole (compound number 48, 0.95 g) as a white solid, m.p. 152–155.5° C.

By proceeding in a similar manner the following compounds of the invention were prepared:

5-cyclopropyl-4-[2-N-ethyl-N-methoxycarbonylamino)-3-fluoro-4-methylsulphonylbenzoyl]isoxazole (compound number 49), m.p. 127.5–131° C. (from compound 37).

5-cyclopropyl-4-[2-(N-ethyl-N-methoxycarbonylamino)-3-fluoro-4-methylsulphinylbenzoyl]isoxazole (compound number 50), m.p. 43–48° C. (also from compound 37).

Reference Example 1

A mixture of 1-[4-chloro-2-(N-methylacetamido)phenyl]-3-cyclopropane-1,3-dione (0.3 g) and N,N-diethylformamide dimethyl acetal (0.3 ml) was heated in dry toluene at 65° C. for 3 hours. The solution was evaporated to dryness and re-evaporated after addition of toluene to give 1-[4-chloro-2-(N-methyl-acetamido)phenyl]-3-cyclopropyl-2-dimethylamino-methylenepropane-1,3-dione (0.32 g) as a brown oil, which was used directly in the next stage.

By proceeding in a similar manner employing dichloromethane as solvent at reflux for 3 days the following compounds were also prepared from the appropriately substituted starting materials:

1-[4-bromo-3-ethoxy-2-(N-methyl-N-methylsulphonylamino)-phenyl]-3-cyclopropyl-2-dimethylaminomethylenepropane-1,3-dione;

1-[4-chloro-2-(N-ethyl-N-methylsulphonylamino)phenyl]-3-cyclopropyl-2-dimethylaminomethylenepropane-1,3-dione;

3-cyclopropyl-2-dimethylaminomethylene-1-[4-methyl-2-(N-methyl-N-methylsulphonylamino)phenyl]propane-1,3-dione;

1-[4-chloro-2-(N-propyl-N-methylsulphonylamino) phenyl]-3-cyclopropyl-2-dimethylaminomethylenepropane-1,3-dione;

3-cyclopropyl-2-dimethylaminomethylene-1-dione;

3-cyclopropyl-2-dimethylaminomethylene-1-[2-(N-ethyl-N-methylsulphonylamino)-4-methylsulphonylphenyl]-propane-1,3-dione;

1-[3,4-dichloro-2-(N-methyl-N-methylsulphonylamino)-phenyl]-3-cyclopropyl-2-dimethylaminomethylenepropane-1,3-dione;

1-[4-bromo-2-(N-methyl-N-methylsulphonylamino) phenyl]-3-cyclopropyl-2-dimethylaminomethylenepropane-1,3-dione;

3-cyclopropyl-2-dimethylaminomethylene-1-[3,4-difluoro-2-(N-methyl-N-methylsulphonylamino)phenyl]-propane-1,3-dione;

3-cyclopropyl-2-dimethylaminomethylene-1-[4-iodo-2-(N-methyl-N-methylsulphonylamino)phenyl]-propane-1,3-dione; and 1-[2-(N-isobutyl-N-methylsulphonylamino)-4-chlorophenyl]-3-cyclopropyl-2-dimethylaminomethylenepropane-1,3-dione.

Reference Example 2

N-methyl-acetamide (0.24 g) was added to a suspension of sodium hydride (0.4 g, 60% oil dispersion) in dry dioxan (30 ml). To this was added 1-(2-bromo-4-chlorophenyl)-3-cyclopropylpropane-1,3-dione (1.0 g) followed by copper (I) bromide (1.0 g) and the mixture heated at reflux for 7 hours and allowed to stand at ambient temperature for 3 days. After evaporation to dryness the residue was added to dilute hydrochloric acid and extracted (ethyl acetate). The extract was washed (water), dried (magnesium sulphate) and evaporated to dryness. Purification by chromatography gave 1-[4-chloro-2-(N-methylacetamido)phenyl]-3-cyclopropane-1,3-dione (0.32 g) as an orange solid, m.p. 110–112° C.

Reference Example 3

Cyclopropylmethylketone (4.0 g) was added to a suspension of sodium hydride (3.2 g, 60% oil dispersion) in dry tetrahydrofuran (10 ml). When the evolution of hydrogen had subsided, a solution of methyl 2-bromo-4-chlorobenzoate (10.0 g) in tetrahydrofuran was added dropwise. The resulting mixture was heated at reflux overnight, cooled, evaporated to dryness and poured onto dilute hydrochloric acid. The mixture was extracted (dichloromethane), dried (magnesium sulphate) and evaporated to give, after purification by chromatography, 1-(2-bromo-4-chlorophenyl)-3-cyclopropyl-propan-1,3-dione (3.07 g), m.p. 42–45° C. as an orange solid.

Reference Example 4

A solution of 1-[3,4-dichloro-2-(N-methyl-methoxycarbonylamino)phenyl]-3-cyclopropane-1,3-dione (2.81 g) and triethylorthoformate (2.42 g) in acetic anhydride (25 g) was heated at reflux for 1.5 hours, cooled and evaporated to dryness to give 1-[3,4-dichloro-2-(N-methyl-methoxycarbonylamino)phenyl]-3-cyclopropyl-2-ethoxymethylenepropane-1,3-dione (3.58 g) which was used directly in the next stage.

By proceeding in a similar manner the following compounds were prepared from the appropriately substituted stating materials:

1-[3,4-dichloro-2-(N-methyl-ethoxycarbonylamino) phenyl]-3-cyclopropyl-2-ethoxymethylenepropane-1,3-dione, isolated as a brown oil.
1-[3,4-dichloro-2-(N-ethyl-methoxycarbonylamino) phenyl]-3-cyclopropyl-2-ethoxymethylenepropane-1,3-dione.
1-[3,4-dichloro-2-(N-methyl-N-isopropyloxycarbonylamino)phenyl]-3-cyclopropyl-2-ethoxymethylenepropane-1,3dione.
1-[4-bromo-3-ethoxy-2-(N-ethyl-N-methoxycarbonylamino)phenyl]-3-cyclopropyl-2-ethoxymethylenepropane-1,3-dione.
1-[4-bromo-2-(N-ethyl-N-methoxycarbonylamino)-3-(2,2,2-trifluoroethoxy)phenyl]-3-cyclopropyl-2-ethoxymethylenepropane-1,3 dione.
1-[4-bromo-2-(N-ethyl-N-methoxycarbonylamino)-3-methoxyphenyl]-3-cyclopropyl-2-ethoxymethylenepropane-1,3dione.
1-[3,4-dichloro-2-(N-propyl-N-methoxycarbonylamino) phenyl]-3-cyclopropyl-2-ethoxymethylenepropane-1,3-dione.
1-[3,4 -dichloro-2-(N-isopropyl-N-methoxycarbonylamino) phenyl]-3-cyclopropyl-2-ethoxymethylenepropane-1,3-dione.
1-[3,4-dichloro-2-(N-alkyl-N-methoxycarbonylamino) phenyl]-3-cyclopropyl-2-ethoxymethylenepropane-1,3-dione.
1-[3,4-dichloro-2-(N-ethyl-N-ethoxycarbonylamino) phenyl]-3-cyclopropyl-2-ethoxymethylenepropane-1,3-dione.
1-[3,4-dichloro-2-(N-ethyl-N-propyloxycarbonylamino) phenyl]-3-cyclopropyl-2-ethoxymethylenepropane-1,3-dione.
1-[3,4-dichloro-2-(N-ethyl-N-isopropyloxycarbonylamino) phenyl]-3-cyclopropyl-2-ethoxymethylenepropane-1,3-dione.
1-[3,4-dichloro-2-(N-ethyl-N-n-butyloxycarbonylamino) phenyl]-3-cyclopropyl-2-ethoxymethylenepropane -1,3-dione.
1-[3,4-dichloro-2-(N-ethyl-N-methoxycarbonylamino) phenyl]-2-ethoxymethylene-3-isopropylpropane-1,3-dione.
3-cyclopropyl-2-ethoxymethylene-1-[2-(N-ethyl-N-methylsulphonylamino)phenyl]propane-1,3-dione.
1-[3-chloro-2-(N-ethyl-N-methylsulphonylamino)-4-(methylthio)phenyl]-3-cyclopropyl-2-ethoxymethylenepropane-1,3-dione.
3-cyclopropyl-2-ethoxymethylene-1-[2-(N-ethyl-N-methylsulphonylamino)-3,4-difluorophenyl]propane-1,3-dione.
3-cyclopropyl-2-ethoxymethylene-1-[2-(N-ethyl-N-methylsulphonylamino)-3-fluoro-4-(methylthio)phenyl] propane-1,3-dione.
1-[4-chloro-2-(N-ethyl-N-methylsulphonylamino)-3-fluorophenyl]-3-cyclopropyl-2-ethoxymethylenepropane-1,3-dione.
1-[3,4-dibromo-2-(N-ethyl-N-methylsulphonylamino) phenyl]-3-cyclopropyl-2-ethoxymethylenepropane-1,3-dione.
3-cyclopropyl-2-ethoxymethylene-1-[2-(N-ethyl-N-methylsulphonylamino)-4-fluorophenyl]propane-1,3-dione.
3-cyclopropyl-2-ethoxymethylene-1-[2-(N-ethyl-N-methylsulphonylamino)-4-trifluoromethylphenyl] propane-1,3-dione.
1-[3-chloro-2-(N-ethyl-N-methylsulphonylamino)phenyl]-3-cyclopropyl-2-ethoxymethylenepropane-1,3-dione.
1-[4-chloro-2-(N-methyl-N-methylsulphonylamino) phenyl]-3-cyclopropyl-2-ethoxymethylenepropane-1,3-dione.
3-cyclopropyl-2-ethoxymethylene-1-[2-(N-propyl-N-methylsulphonylamino)-4-trifluoromethoxyphenyl] propane-1,3-dione.

Reference Example 5

A suspension of 3,4-dichloro-2-(N-ethyl-N-methoxycarbonylamino)benzoyl chloride (3.5 g) in dry toluene was added dropwise during 0.25 hours to a stirred solution of tert-butyl 3-cyclopropyl-3-oxopropionate magnesium enolate (3.5 g) in toluene at room temperature. Stirring was maintained overnight and hydrochloric acid (2M) added. The toluene layer was separated and dried by azeotropic distillation before addition of para-toluenesulphonic acid (0.1 g). The mixture was heated at reflux for 4 hours, allowed to cool, washed (water) and evaporated to dryness. The residue was purified by chromatography to give 1-[3,4-dichloro-2-(N-ethyl-N-methoxycarbonylamino)phenyl]-3-cyclopropylpropane-1,3-dione (2.49 g), NMR 1.0(m,2H), 1.1–1.3(2t,3H), 1.2(m,2H), 1.7(m,1H), 3.4–3.7(2m,2H), 3.6–3.8(2s, 5.9(s,1H), 7.5(m, 2H), 16.0(s,1H).

By proceeding in a similar manner the following compounds were prepared from the appropriately substituted starting materials:

1-[3,4-dichloro-2-(N-methyl-N-ethoxycarbonylamino) phenyl]-3-cyclopropylpropane-1,3-dione as a brown oil, NMR 0.9(m,2H), 1.0.–1.3(2t,3H),1.1(m,2H), 3.1(s,3H), 4.1–4.2(2m,2H), 5.9(s,1H), 7.5(m,2H), 16.0(s,1H).

1-[3,4-chloro-2-(N-methyl-N-methoxycarbonylamino) phenyl]-3-cyclopropylpropane-1,3-dione as a brown gum, NMR 0.9(m,2H), 1.1(m,2H), 1.6(m,1H), 3.0(s,3H), 3.5 and 3.7(2s,3H), 5.8(s,1H), 7.4(m,2H), 16.0(s,1H).

1-[3,4-dichloro-2-(N-methyl-N-isopropyloxycarbonylamino)phenyl]-3-cyclopropylpropane-1,3-dione, NMR 1.0(m,2H), 1.1(m,6H), 1.2(m,2H), 1.7(m,1H), 3.1(s,1H), 4.95(m,1H), 5.9(s,1H), 7.5(s,2H), 15.95(s,1H).

3-cyclopropyl-1-[2-(N-ethyl-N-methylsulphonylamino)-4-fluorophenyl]propane-1,3-dione, NMR 1.0(m,2H), 1.15(t,3H), 1.2(m,2H), 1.8(m,1H), 3.0(s,3H), 3.55(m,6H), 6.1(s,1H), 7.2(m,2H), 7.6(t,1H), 16.2(s,1H).

1-[4-bromo-3-ethoxy-2-(N-ethyl-N-methoxycarbonylamino)phenyl]-3-cyclopropylpropane-1,3-dione, NMR 1.0(m,2H), 1.15(m,5H), 1.4(m,3H), 1.7(m,1H), 3.6(s,3H), 3.75(q,2H), 4.0(m,2H), 5.9(s,1H), 7.25(d,1H), 7.55(d,1H).

1-[4-bromo-2-(N-ethyl-N-methoxycarbonylamino)-3-(2,2-trifluoroethoxy)phenyl]-3-cyclopropylpropane-1,3-dione, NMR 1.1(m,8H), 1.7(m,1H), 3.6(s,3H), 3.65(m,2H), 4.2(m,1H), 4.5(m,1H), 5.85(s,1H), 7.35(d,1H), 7.6(d,1H), 16.0(s,1H).

1-[4-bromo-2-(N-ethyl-N-methoxycarbonylamino)-3-methoxyphenyl]-3-cyclopropylpropane-1,3-dione, NMR 1.1(m,7H), 1.7(m,1H), 3.6(m,4H), 3.85(t,4H), 5.85(s,1H), 7.25(d,1H), 7.6(d1H).

3-cyclopropyl-1-[2-(N-ethyl-N-methylsulphonylamino)phenyl]propane-1,3-dione, NMR 1.0(m,2H), 1.2(m,2H), 1.25(t,3H), 1.75(m,1H), 3.0(s,3H), 3.65(m,2H), 6.1(s,1H), 7.4(m,2H), 7.5(m,1H), 7.6(m,1H), 16.1(brs,1H).

1-[3-chloro-2-(N-ethyl-N-methylsulphonylamino)-4-(methylthio)phenyl]-3-cyclopropylpropane-1,3-dione, m.p. 101–102° C.

3-cyclopropyl-1-[2-(N-ethyl-N-methylsulphonylamino)-3,4-difluorophenyl]propane-1,3-dione, NMR 1.05(m,2H), 1.15(t,3H), 1.2(m,2H), 1.8(m,1H), 3.1(s,3H), 3.6(q,2H), 6.75(s,1H), 7.25(m,1H), 7.45(m,1H), 16.1(brs,1H).

3-cyclopropyl-1-[2-(N-ethyl-N-methylsulphonylamino)-3-fluoro-4-(methylthio)phenyl]propane-1,3-dione, NMR 1.0 (m,2H), 1.2(m,2H), 1.25(t,3H), 1.8(m,1H), 2.5(s,3H), 3.1(s,3H), 3.6(q,2H), 6.3(s, 1H), 7.25(m,1H), 7.5(m,1H), 16.15 (brs, 1H).

1-[4-chloro-2-(N-ethyl-N-methylsulphonylamino)-3-fluorophenyl]-3-cyclopropylpropane-1,3-dione, NMR 1.0 (m,2H), 1.15(t,3H), 1.2(m,2H), 3.1(s,3H), 3.6(q,2H), 6.25 (s,1H), 7.5(m,2H), 16.0(brs,1H).

1-[3,4-dibromo-2-(N-ethyl-N-methylsulphonylamino)phenyl]-3-cyclopropylpropane-1,3-dione, NMR 1.2(m,7H), 1.75(m,1H), 3.05(s,3H), 3.75(m,2H), 6.0(s,1H), 7.3(d,1H), 7.7(d,1H).

1-[3-chloro-2-(N-ethyl-N-methylsulphonylamino)phenyl]-3-cyclopropylpropane-1,3-dione, NMR 1.0(m,2H), 1.15(m,5H), 1.7(m,1H), 3.0(s,3H), 3.65(m,2H), 6.0(s,1H), 7.3(t,1H), 7.4(d,1H), 7.5(d,1H), 15.9(brs,1H).

1-[3,4-dichloro-2-(N-propyl-N-methoxycarbonylamino)phenyl]-3-cyclopropylpropane-1,3-dione, NMR 0.85(t,3H), 1.0(t,2H), 1.2(t,2H), 1.55(m,2H), 1.7(m,1H), 3.25(m,2H), 3.7(s,3H), 5.85(s,1H), 7.5(m,2H), 15.9(brd,1H).

1-[3,4-dichloro-2-(N-isopropyl-N-methoxycarbonylamino)phenyl]-3-cyclopropylpropane-1,3-dione, NMR 1.1(m,10H), 1.7(m,1H), 3.7(s,3H), 4.25(m,1H), 5.85(s,1H), 7.45(m,2H), 15.8(brd,1H).

1-[4-dichloro-2-(N-allyl-N-methoxycarbonylamino)phenyl]-3-cyclopropylpropane-1,3-dione, NMR 1.0(m,2H), 1.2(m,2H), 1.75(m,1H), 2.35(s,2H), 3.7(s,3H), 4.05(m,1H), 5.0(t,2H), 5.85(s,2H), 7.25(m,1H), 7.45(m,2H), 15.9(brd, 1H).

1-[3,4-chloro-2-(N-ethyl-N-propyloxycarbonylamino)phenyl]-3-cyclopropylpropane-1,3-dione, NMR 1.0(m, 2H), 1.2(m,2H), 1.3(t,3H), 1.7(m,1H), 4.2(q,2H), 6.07 (s,1H), 7.4(d,1H), 7.46(d,1H), 16.05(brs,1H).

1-[3,4-dichloro-2-(N-ethyl-N-ethoxycarbonylamino)phenyl]-3-cyclopropylpropane-1,3-dione, NMR 1.0–1.2(m, 10H), 1.7(m,1H), 3.45(m,1H), 3.73(m,1H), 4.2(m,2H), 5.88 (s,1H), 7.5(s,2H), 15.9(brs, 1H).

1-[3,4-dichloro-2-(N-ethyl-N-isopropyloxycarbonylamino)phenyl]-3-cyclopropylpropane-1,3-dione, NMR 1.0–1.2(m,8H), 1.35 (m,2H), 1.59(m,1H), 3.42(m,1H), 3.7(m,1H), 5.03(m,1H), 5.88(s,1H), 75(s,2H), 15.88(brs,1H).

1-[3,4-dichloro-2-(N-ethyl-N-n-butyloxycarbonylamino)phenyl]-3-cyclopropylpropane-1,3-dione, NMR 0.84(t,3H), 1.0–1.26(m,9H), 1.5(m,2H), 1.7(m,1H), 3.42(m,1H), 3.73 (m,1H), 4.11(t,2H), 5.88(s,1H), 7.5(s,2H), 15.95(brs,1H).

1-[3,4-dichloro-2-(N-ethyl-N-methoxycarbonylamino)phenyl]-3-isopropylpropane-1,3-dione, NMR 1.08(t,3H), 1.2(d,6H), 2.58(m,1H), 3.47(m,1H), 3.7(m,1H), 3.7(s,3H), 5.8(s,1H), 7.5(s,2H), 15.6(brs,1H).

1-[4-chloro-2-(N-methyl-N-methylsulphonylamino)phenyl]-3-cyclopropylpropane-1,3-dione, 93.3–96.5° C.

1-[4-chloro-2-(N-ethyl-N-methylsulphonylamino)phenyl]-3-cyclopropylpropane-1,3-dione, NMR 0.9–1.4(m, 7H), 1.07–1.9(m,1H), 3.0(s,3H), 3.65(q,2H), 6.1(s,1H), 7.4 (m,2H), 7.55(d,1H), 16.0–16.3(brs,1H).

3-cyclopropyl-1-[4-methyl-2-(N-methyl-N-methylsulphonylamino)phenyl]propane-1,3-dione, NMR 0.9–1.1(m,2H), 1.15–1.25(m,2H), 1.7–1.85(m,1H), 2.35(s, 3H), 2.95(s,3H), 3.25(s,3H), 6.1(s,1H), 7.15(d,1H), 7.2(s, 1H), 7.5(d,1H), 16.1–16.3(brs,1H).

1-[4-2-chloro-2-(N-propyl-N-methylsulphonylamino)phenyl]-3-cyclopropylpropane-1,3-dione, NMR 0.9(t,3H), 1.05(m,2H), 1.25(m,2H), 1.45–1.65(m,4H), 1.78(m,1H), 3.03(s,3H), 6.15(s,1H), 7.38–7.48(m,2H), 7.57(dd,1H), 16.12(brs,1H).

3-cyclopropyl-1-[2-(N-ethyl-N-methylsulphonylamino)-4-methylsulphonylphenyl]propane-1,3-dione, NMR 1.0–1.3 (m,7H), 1.79(m,1H), 3.0(s,3H), 6.15(s,1H), 7.78(d,1H), 7.98(m,2H).

1-[3,4-chloro-2-(N-methyl-N-methylsulphonylamino)phenyl]-3-cyclopropylpropane-1,3-dione.

3-cyclopropyl-1-[2-(N-methyl-N-methylsulphonylamino)-4-trifluoromethylphenyl]propane-1,3-dione.

3-cyclopropyl-1-[2-(N-methyl-N-methylsulphonylamino)-4-trifluoromethoxyphenyl]propane-1,3-dione, NMR 1.0(m,2H), 1.2(m,1H), 1.7(m,1H), 3.0(s,3H), 3.25(s,3H), 6.05(s,1H), 7.25(m,2H), 7.6(d,1H), 16.0(s,1H).

3-cyclopropyl-1-[4-iodo-2-(N-methyl-N-methylsulphonylamino)phenyl]propane-1,3-dione, m.p. 131.5–134.° C.

Reference Example 6

Sodium hydroxide solution (2M, 44.6ml) was added dropwise during 5 minutes to a stirred solution of methyl 3,4-dichloro-2-(N-methyl-N-ethoxycarbonylamino) benzoate (9.1 g) in methanol. After 0.5 hours the methanol was evaporated, the residue diluted (water), washed (ether), acidified with potassium bisulphate and extracted (ethyl acetate). The extract was dried (magnesium sulphate) and evaporated to give 3,4-dichloro-2-(N-methyl-ethoxycarbonylamino)benzoic acid (9.38 g) as a brown oil, NMR 1.2(m,3H), 3.1(s,3H), 4.0(m,2H), 7.4(m,1H), 7.9(m,1H).

By proceeding in a similar manner the following compounds were prepared from the appropriately substituted starting materials:

3,4-dichloro-2-(N-ethyl-N-methoxycarbonylamino) benzoic acid as a yellow oil, NMR 1.0 and 1.2(2t,3H), 3.5 and 3.8(2s,3H), 3.6 and 4.1(2q,2H), 7.5(m,1H), 7.8(m,2H).

3,4-dichloro-2-(N-methyl-N-methoxycarbonylamino) benzoic acid, NMR 3.1(s,3H), 3.6 and 3.8(2s,3H), 7.5(m, 1H), 7.9(m,1H), 10.0(s,1H).

3,4-dichloro-2-(N-methyl-N-isopropyloxycarbonylamino acid, NMR 1.1(m,6H), 1.3(m,2H), 3.2(s,3H), 4.9(m,1H), 7.55(d,1H), 7.9(d,1H).

4-bromo-3-ethoxy-2-(N-ethyl-N-methylsulphonylamino) benzoic acid, m.p. 195–198° C.

2,4-dibromo-3-ethoxybenzoic acid, m.p. 161–162° C.

4-bromo-3-ethoxy-2-(N-ethyl-N-methoxycarbonylamino)benzoic acid as an orange solid, m.p. 105–108° C.

2,4-dibromo-3-(2,2,2-trifluoroethoxy)benzoic acid as a white solid, m.p. 147–151° C.

4-bromo-2-(N-ethyl-N-methoxycarbonylamino)-3-methoxybenzoic acid, NMR 1.1(m,3H), 3.65(m,8H), 6.3(s, 1H), 7.55(d,1H), 7.65(d,1H).

2-(N-ethyl-N-methylsulphonylamino)-3-fluoro-4-(methylthio)benzoic acid, m.p. 129–134° C.

4-chloro-2-(N-ethyl-N-methylsulphonylamino)-3-fluorobenzoic acid, m.p. 102.5–100° C.

3,4-dibromo-2-(N-ethyl-N-methylsulphonylamino) benzoic acid, m.p. 110–114° C.

3,4-dichloro-2-(N-ethyl-N-methylsulphonylamino) benzoic acid, m.p. 87–89° C.

3,4-dichloro-2-(N-propyl-N-methoxycarbonylamino) benzoic acid, NMR (DMSO-D$_6$) 0.8(t,3H), 1.5(m,2H), 3.2 (m,2H), 3.5(s,3H), 7.7(d,1H), 7.8(d,1H), 13.5(brd,1H).

3,4-dichloro-2-(N-isopropyl-N-methoxycarbonylamino) benzoic acid, NMR (DMSO-D$_6$) 1.0(d,3H), 3.45(s,3H), 4.15 (m,1H), 7.75(m,2H), 13.0(brd,1H).

3,4-dichloro-2-(N-alkyl-N-methoxycarbonylamino) benzoic acid, NMR (DMSO-D$_6$) 3.5(s,3H), 4.1(m,2H), 5.05 (m,2H), 5.8(m,1H), 7.7(d,1H), 7.85(d,1H), 13.35(brd,1H).

3,4-dichloro-2-(N-ethyl-N-propyloxycarbonylamino) benzoic acid, NMR 0.68(t,3H), 1.07(t,3H), 1.4(q,2H), 3.5–3.7(m,2H), 3.95(m,2H), 7.45(d,1H), 7.87(d,1H), 8.8 (brs,1H).

3,4-dichloro-2-(N-ethyl-N-ethoxycarbonylamino) benzoic acid, NMR 1.1(m,6H), 3.7(m,2H), 4.13(q,2H), 755 (d,1H), 7.92(d,1H), 8.75(brs,1H).

3,4-dichloro-2-(N-ethyl-N-isopropyloxycarbonylamino) benzoic acid, NMR 1.0(m,9H), 3.5–3.7(m,2H), 4.88(m,1H), 7.48(d,1H), 7.85(d,1H).

3,4-dichloro-2-(N-ethyl-N-n-butyloxycarbonylamino) benzoic acid, NMR 0.8(t,3H), 1.1(m,5H), 1.45(m,2H), 3.6–3.8(m,2H), 4.05(m,2H), 6.45(brs,1H), 7.54(d,1H), 7.93 (d,1H).

4-chloro-2-(N-methyl-N-methylsulphonylamino)benzoic acid, m.p. 161–164° C.

4-bromo-3-ethoxy-2-(N-ethyl-N-methylsulphonylamino) benzoic acid, m.p. 117–119° C.

4-bromo-2-(N-ethyl-N-methylsulphonylamino)-3-(2,2,2-trifluoroethoxy)benzoic acid, m.p. 162–164° C.

4-chloro-2-(N-ethyl-N-methylsulphonylamino)benzoic acid, m.p. 148–151° C.

2-(N-ethyl-N-methylsulphonylamino)-4-fluorobenzoic acid, NMR (CD$_3$CN) 1.1(t,3H), 2.95(s,3H), 3.7(q,2H), 7.25 (m,2H), 8.0(t, 1H).

2-(N-ethyl-N-methylsulphonylamino)-4-trifluoromethylbenzoic acid, NMR (CD$_3$CN) 1.1(t,3H), 3.0 (s,3H), 3.7(q,2H), 5.7(brs,1H), 7.8(m,2H), 8.0(d,1H).

3-chloro-2-(N-ethyl-N-methylsulphonylamino)-4-(methylthio)benzoic acid, m.p. 175–176.5° C.

4methyl-2-(N-methyl-N-methylsulphonylamino)benzoic acid m.p. 185–187° C.

4-chloro-2-(N-methylsulphonyl-N-propylamino)benzoic acid, m.p. 133–135° C.

3,4-dichloro-2-(N-methyl-N-methylsulphonylamino) benzoic acid, m.p. 118–119.4° C.

2-(N-methyl-N-methylsulphonylamino)-4-trifluoromethylbenzoic acid, m.p. 157–160° C.

4-bromo-2-(N-methyl-N-methylsulphonylamino)benzoic acid, m.p. 181–182° C.

3,4-difluoro-2-(N-methyl-N-methylsulphonylamino) benzoic acid, m.p. 159.5–161° C.

2-(N-methyl-N-methylsulphonylamino)-4-trifluoromethoxybenzoic acid, m.p. 138.5–141° C.

4-chloro-2-(N-isobutyl-N-methylsulphonylamino) benzoic acid, m.p. 158–159° C.

4-bromo-2-(N-ethyl-N-methylsulphonylamino)-3-methoxybenzoic acid, NMR 1.15(t,3H), 3.1(s,3H), 3.7(m, 2H), 4.1(s,3H), 7.65(q,2H).

2-(N-ethyl-N-methylsulphonylamino)-3,4-difluorobenzoic acid, NMR (DMSO-D$_6$) 1.1(t,3H), 3.1(s, 3H), 3.6(q,2H), 7.6(m,1H), 7.75(m,1H).

Reference Example 7

A solution of 3,4-dichloro-2-(ethoxycarbonylamino) benzoic acid (13.1 g) was stirred with potassium carbonate (26.8 g) in acetone. Methyl iodide (95 ml) was added and the mixture heated at reflux for 2.5 hours, left at room temperature overnight, filtered and the filtrate evaporated to dryness. Purification by chromatography gave methyl 3,4-dichloro-2-(N-methyl-N-ethoxycarbonylamino)benzoate (9.79 g) as a brown oil, NMR 1.0(t,3H), 3.1(2s,3H), 3.8(2s,3H), 4.0(m, 2H), 7.4(m,1H) and 7.7(m,1H).

By proceeding in a similar manner the following compounds were prepared from the appropriately substituted starting materials:

ethyl 3,4-dichloro-2-(N-ethyl-N-methoxycarbonylamino) benzoate, NMR 1.1(t,3H), 1.38(t,3H), 3.62(s,3H), 3.6(m, 2H), 4.36(q,2H), 7.5(d,1H), 7.8(d,1H);

methyl 3,4-chloro-2-(N-methyl-N-methoxycarbonylamino)benzoate, NMR 3.2(2s,3H), 3.6 and 3.8(2s,3H), 3.9(2s,3H), 7.5(m,1H), 7.8(m,1H);

methyl 3,4-chloro-2-(N-methyl-N-isopropyloxycarbonylamino)benzoate, NMR 1.09(m,6H), 3.1(s,3H), 3.8(s3H), 4.9(m,1H), 7.5(m,1H), 7.8(m,1H);

propyl 3,4-chloro-2-(N-propyl-N-methoxycarbonylamino)benzoate, NMR 0.83(t,3H), 0.99(t, 3H), 1.51(m,2H), 1.75(m,2H), 3.45(m,2H), 3.61(s,3H), 4.21 (m,2H), 7.5(d,1H), 7.79(d,1H);

isopropyl 3,4-dichloro-2-(N-isopropyl-N-methoxycarbonylamino)benzoate, NMR 1.0(d,3H), 3.6(s, 3H), 4.25(m,1H), 5.2(m,1H), 7.5(d,1H), 7.75(d,1H);

allyl 3,4-chloro-2-(N-allyl-N-methoxycarbonylamino) benzoate, NMR 3.6(s,3H), 4.2(m,2H), 4.75(m,3H), 5.0(d, 3H), 5.9(m,2H), 7.5(d,1H), 7.8(d,1H);

ethyl 3,4-dichloro-2-(N-ethyl-N-propyloxycarbonylamino)benzoate, NMR 0.75(t,3H), 1.1(t, 3H), 1.37(t,3H), 1.5(q,2H), 3.55(m,2H), 3.7(m,2H), 4.0(m, 2H), 4.35(q,2H), 7.52(d,1H), 7.8(d,1H);

ethyl-3,4-dichloro-2-(N-ethyl-N-ethoxycarbonylamino) benzoate, NMR 1.1(m,6H), 1.37(t,3H), 3.5–3.75(m,2H), 4.1 (m,2H), 4.37(q,2H), 7.5(d,1H), 7.8(d,1H);

ethyl-3,4-dichloro-2-(N-ethyl-N-isopropyloxycarbonylamino)benzoate, NMR 1.07(m,9H), 1.37(t,3H), 3.53(m,1H).

ethyl 3,4-dichloro-2-(N-ethyl-N-n-butyloxycarbonylamino)benzoate, NMR 0.8(t,3H), 1.09(t, 3H), 1.16(m,2H), 1.38(t,3H), 1.46(m,2H), 3.56(m,1H), 3.7 (m,1H), 4.02(m,2H), 4.32(q,2H), 7.5(d,1H), 7.8(d, 1H);

Reference Example 8

A suspension of 2-amino-3,4-dichlorobenzoic acid (10.0 g) in saturated sodium carbonate solution (80 ml) was diluted with water and filtered. The stirred filtrate was treated by dropwise addition of ethyl chloroformate. After 1 hour additional sodium carbonate solution (80 ml) and ethyl chloroformate (9.28 ml) were added and the mixture stirred for 1 hour. Potassium bisulphate solution was added to pH2 and the mixture extracted (ethyl acetate), dried (magnesium sulphate) and evaporated to give 3,4-dichloro-2-ethoxycarbonylaminobenzoic acid (13.14 g), NMR ($D_6$-DMSO)1.2(t,3H), 4.1(m,2H), 7.6(d,1H), 7.7(d,1H), 9.4(s, 1H).

By proceeding in a similar manner the following compounds were prepared from the appropriately substituted staring materials:

3,4-dichloro-2-methoxycarbonylaminobenzoic acid, NMR ($CD_3CN$) 3.7(s,3H), 7.5(d,1H), 7.8(d,1H);

methyl bromo-3-ethoxy-2-(N-ethyl-N-methoxycarbonylamino)benzoate, NMR 1.1(t,3H), 1.4(t, 3H), 3.6(s,3H), 4.0(m,6H), 7.6(s,2H) (n.b. in this case the methyl ester was obtained rather than the acid);

4-bromo-2-(N-ethyl-N methoxycarbonylamino)-3-(2,2,2-trifluoroethoxy)benzoic acid, NMR (DMSO-$D_6$) 1.0(t,3H), 1.4(s,3H), 1.5(s,2H), 3.6(m,2H), 3.7(s,1H), 4.35(m,1H), 4.6 (m,1H), 7.65(s,2H);

methyl 4-bromo-2-(N-ethyl-N-methoxycarbonylamino)-3-methoxybenzoate, NMR 1.1(m,3H), 3.6(m,4H), 3.8(m, 6H), 3.9(m,2H), 7.6(s,2H) (n.b. in this case the methyl ester was obtained rather than the acid);

3,4-dichloro-2-propyloxycarbonylaminobenzoic acid, m.p. 156–160° C.;

3,4-dichloro-2-isopropyloxycarbonylaminobenzoic acid, m.p. 188–190° C.;

2-n-butyloxycarbonylamino-3,4-dichlorobenzoic acid, m.p. 128–130° C.

Reference Example 9

Magnesium (3.0 g) was stirred in methanol, carbon tetrachloride (0.5 ml) added and the mixture warmed at 50° C. until the metal had dissolved (1.5 hours). Tert-butyl 3-cyclopropyl-3-oxopropanoate (20.0 g) was then added dropwise and the mixture heated under reflux conditions for 1 hour. The solvent was evaporated and re-evaporated after addition of toluene to give tert-butyl 3-cyclopropyl-3-oxopropanoate magnesium salt (29.9 g) as a white solid, m.p. >300° C., IR max (C=O) 1520, 1540; (C—O) 1350 cm-1.

Reference Example 10

A mixture of 4-[4-bromo-3-ethoxy-2-(N-methyl-N-methylsulphonylamino)benzoyl]-5-cyclopropylisoxazole (0.5 g) and concentrated sulphuric acid (6 ml) in acetic acid (9 ml) was heated at 70° C. for 4 hours, then at 90° C. for 4 hours. The mixture was poured into excess water and carefully brought to pH 5.5 by the addition of 2M sodium hydroxide solution. extracted with ethyl acetate, dried (anhydrous magnesium sulphate), evaporated and purified by column chromatography to yield 4-[4-bromo-3-ethoxy-2-(methylamino)benzoyl]-5-cyclopropylisoxazole (0.096 g), NMR 1.15(m,2H), 1.25(m,2H), 1.4(t,3H), 2.5(m,1H), 2.9(s,3H), 3.9(q,2H), 6.8(d,1H), 7.05(d,1H), 7.1(s,1H), 8.25 (s,1H).

By proceeding in a similar manner the following compounds were prepared from the appropriately substituted starting materials:

4-[4-chloro-2-(methylamino)benzoyl]-5-cyclopropylisoxazole, NMR 1.1(m,2H), 1.2(m,2H), 2.3(m, 1H), 2.9(m,3H), 6.5(q,1H), 6.6(d,1H), 7.4(d,1H), 8.2(s,1H), 8.4(brs,1H);

4-[3,4-difluoro-2-(methylamino)benzoyl]-5-cyclopropylisoxazole, NMR 1.2(m,2H), 1.3(m,2H), 2.45(m, 1H), 3.2(m,3H), 6.45(m,1H), 73(m,1H), 8.2(s,1H), 8.3(s, 1H);

4-[4-chloro-2-(ethylamino)benzoyl]-5-cyclopropylisoxazole, NMR 1.2(m,2H), 1.3(m,5H), 2.4(m, 1H), 3.2(m,2H), 6.6(d,1H), 6.7(s,1H), 7.5(d,1H), 8.3(s,1H), 8.45(s,1H);

4-[4-chloro-2-(propylamino)benzoyl]-5-cyclopropylisoxazole, NMR 1.05(t,3H), 1.21(m, 2H), 1.3 (m,2H), 1.8(q,2H), 2.45(m,1H), 3.2(m,2H), 6.6(d,1H), 7.5 (d,1H), 8.3(s,1H), 8.6(s,1H);

5-cyclopropyl-4-(2-ethylamino-4-fluorobenzoyl) isoxazole, NMR 1.2(m,2H), 1.35(m,5H), 2.4(m,1H), 3.25 (m,2H), 6.3(m,2H), 7.6(h,1H), 8.4(s,1H), 8.6(s,1H), 5-cyclopropyl-4-(2-ethylamino-4-trifluoromethylbenzoyl)isoxazole, NMR 1.2(m,2H), 1.35(m, 5H), 2.5(m,1H), 3.3(m,2H), 6.8(d,1H), 7.0(s,1H), 7.7(d,1H), 8.3(s,1H), 8.35(s,1H);

5-cyclopropyl-4-(2-methylamino-4-trifluoromethylbenzoyl)isoxazole, NMR 1.1(m,2H), 1.2(m, 2H), 2.4(m,1H), 2.9(d,3H), 6.8(q,1H), 6.9(s,1H), 7.6(d,1H), 8.2(s,2H);

4-[4-bromo-2-(methylamino)benzoyl]-5-cyclopropylisoxazole, NMR 1.1(m,2H), 1.2(m,2H), 2.4(m, 1H), 2.8(s,3H), 6.6(q,1H), 6.8(s,1H), 7.3(d,1H), 8.2(s,2H);

5-cyclopropyl-4-[4-iodo-2-(methylamino)benzoyl] isoxazole, NMR 1.1(m,2H), 1.2(m,2H), 2.3(m,1H), 2.8(s, 3H), 6.9(q,1H), 7.1(s,1H), 7.2(d,1H), 8.2(s,2H);

5-cyclopropyl-4-(2-methylamino-4-trifluoromethoxybenzoyl)isoxazole, NMR 1.1(m,2H), 1.2 (m,2H), 2.4(m,1H), 2.9(d,3H), 6.4(q,1H), 6.5(s,1H), 7.5(d, 1H), 8.2(s,1H), 8.5(brs,1H);

4-[4-chloro-2(isobutylamino)benzoyl]-5-cyclopropylisoxazole, NMR 0.9(d,6H), 1.1(m,2H), 1.2(m, 2H), 1.9(m,1H), 2.4(m,1H), 3.0(t,2H), 6.4(q,1H), 6.5(s,1H), 7.4(d, 1H), 8.2(s,1H), 8.6(s,1H);

4-[3,4-dichloro-2-(methylamino)benzoyl]-5-cyclopropylisoxazole, NMR 1.2(m,2H), 1.3(m,2H), 2.6(m, 1H), 2.8(s,3H), 5.6(brs,1H), 6.8(d,1H), 7.2(d,1H), 8.12(s, 1H);

5-cyclopropyl-4-[4-methyl-2-(methylamino)benzoyl] isoxazole, NMR 1.1(m,2H), 1.2(m,2H), 2.2(s,3H), 2.3(m, 1H), 2.8(s,3H), 6.3(q,1H), 6.5(s,1H), 7.4(d,1H), 8.2(s,1H), 8.9(brs,1H);

5-cyclopropyl-4-(2-ethylamino-4-methylsulphonylbenzoyl)isoxazole, NMR 1.1(m,2H), 1.2

(m,5H), 2.5(m,1H), 3.0(s,3H), 3.2(m,2H), 7.0(d,1H), 7.2(m, 1H), 7.6(d,1H), 8.2(brs,1H), 8.3(s,1H);

5-cyclopropyl-4-[(2-ethylamino)benzoyl]isoxazole, NMR 1.15(m,2H), 1.3(m,2H), 1.35(t,3H), 2.45(m,1H), 3.3 (q,2H), 6.6(dt,1H), 6.75(d,1H), 7.4(m,1H), 7.55(dd,1H), 83(s,2H);

4-[3-chloro-2-ethylamino-4-(methylthio)benzoyl]-5-cyclopropylisoxazole, NMR 1.2(t,3H), 1.25(m,2H), 1.35(m, 2H), 2.5(s,3H), 2.65(m,1H), 3.15(m,2H), 5.6(brs,1H), 6.6(d, 1H), 7.35(d,1H), 8.3(s,1H);

5-cyclopropyl-4-(2-ethylamino-3,4-difluorobenzoyl) isoxazole, NMR 1.2(m,2H), 1.3(m,5H), 2.45(m,1H), 3.6(m, 2H), 6.4(m,1H), 7.3(m,1H), 8.2(brs,1H), 8.3(s,1H);

5-cyclopropyl-4-[2-ethylamino-3-fluoro-4-(methylthio) benzoyl]isoxazole, NMR 1.2(m,2H), 1.25(t,3H), 1.3(m,2H), 2.5(m,4H), 3.55(m,2H), 6.45(dd,1H), 7.3(dd,1H), 8.0(brs, 1H), 8.3(s,1H);

4-(4-chloro-2-ethylamino-3-fluorobenzoyl)-5-cyclopropylisoxazole, m.p. 105.5–107° C.;

4-[3,4-dibromo-2-(ethylamino)benzoyl]-5-cyclopropylisoxazole, m.p. 93–95° C.;

4-[3-chloro-2-(ethylamino)benzoyl]-5-cyclopropylisoxazole, NMR 1.15(t,3H), 1.25(m,4H), 2.7(m, 1H), 3.1(m,2H), 5.25(s,1H), 6.8(t,1H), 7.3(d,1H), 7.45(d, 1H), 8.3(s,1H).

Reference Example 11

A suspension of 4-bromo-3-ethoxy-2-(N-methyl-N-methylsulphonylamino)benzoyl chloride (2.45 g) in toluene (35 ml) was added to a solution of tert-butyl 3-cyclopropyl-3-oxopropionate magnesium enolate (1.3 g) in toluene (15 ml) and stirred for 2 days. Trifluoroacetic acid (1.1 ml) was added and the mixture was warmed at 65° C. for 1.5 hours, then cooled, washed with water, the organic extract dried (anhydrous magnesium sulphate) and the solvent evaporated. Purification by chromatography gave 1-[4-bromo-3-ethoxy-2-(N-methyl-N-methylsulphonylamino)phenyl]-3-cyclopropylpropane-1,3-dione (1.87 g) as a yellow semi-solid, NMR 1.05(m,2H), 1(m,2H), 1.5(t,3H), 1.75(m,1H), 3.0(s,3H), 3.3(s,3H), 4.2(brm,2H), 6.1(s,1H), 7.15(d,1H), 7.6(d,1H), 15.9(brs,1H).

By proceeding in a similar manner the following compounds were prepared from the appropriately substituted starting materials:

1-[4-bromo-2-(N-methyl-N-methylsulphonylamino) phenyl]-3-cyclopropylpropane-1,3-dione, m.p. 120–122° C.;

1-[4-chloro-2-(N-isobutyl-N-methylsulphonylamino) phenyl]-3-cyclopropylpropane-1,3-dione, NMR 0.9(m,6H), 1.01(m,2H), 1.25(m,2H), 1.8(m,1H), 3.05(s,3H), 3.45(brs, 2H), 6.1(s,1H), 7.3(m,3H), 16.1(brs,1H);

3-cyclopropyl-1-[3,4-difluoro-2-(N-methyl-N-methylsulphonylamino)phenyl]propane-1,3-dione.

Reference Example 12

4-Bromo-3-ethoxy-2-(N-methylsulphonylamino)benzoic acid (2.83 g) was added to a suspension of potassium carbonate (7.0 g) in dry acetone and heated under reflux for 1.25 hours. Methyl iodide (6.2 ml) was added and the mixture was heated for a further 45 hours. The cooled mixture was filtered and the filtrate evaporated. After addition of dichloromethane, the solution was washed with sodium bicarbonate solution, water, dried (anhydrous magnesium sulphate) and the solvent evaporated to give methyl 4-bromo-3-ethoxy-2-(N-methyl-N-methylsulphonylamino) benzoate (2.91 g), m.p. 82–88° C.

By proceeding in a similar manner the following compounds were prepared from the appropriately substituted starting materials:

ethyl 2-(N-ethyl-N-methylsulphonylamino)-4-fluorobenzoate, NMR 1.2(t,3H), 1.4(t,3H), 3.0(s,3H), 3.7(m, 2H), 4.4(q,2H), 7.15(m,2H), 8.0(t,1H);

ethyl 2-(N-ethyl-N-methylsulphonylamino)-4-trifluoromethylbenzoate, propyl 4-chloro-2-(N-methylsulphonyl-N-propylamino) benzoate m.p. 81–83° C.;

ethyl 2-(N-ethyl-N-methylsulphonylamino)-4-methylsulphonylbenzoate m.p. 108.6–109.4° C.;

methyl 2-(N-methyl-N-methylsulphonylamino)-4-trifluoromethylbenzoate, NMR 2.93(s,3H), 3.3(s,3H), 3.9(s, 3H), 7.65(m,2H), 8.0(dd, 1H);

methyl 4-bromo-2-(N-methyl-N-methylsulphonylamino) benzoate, NMR 2.95(s,3H), 3.23(s,3H), 3.83(s,3H), 7.5(dd, 1H), 7.58(d,1H), 7.75(d,1H);

methyl 4-methyl-2-(N-methyl-N-methylsulphonylamino) benzoate m.p. 100–103° C.;

methyl 3,4-difluoro-2-(N-methyl-N-methylsulphonylamino)benzoate as an orange solid, NMR 3.01(s,3H), 3.3(s,3H), 3.91(s,3H), 7.24(q,1H), 7.73(m,1H).

Reference Example 13

Methanesulphonamide (1.05 g) was added to a suspension of sodium hydride (60% oil dispersion, 1.36 g) in dry dioxan. 2,4-Dibromo-3-ethoxybenzoic acid (4.0 g) was added, followed by copper (I) bromide (0.16 g) and the mixture was heated under reflux for 15 hours. The cooled mixture was concentrated, 2M hydrochloric acid solution added, and extracted with ethyl acetate. The organic phase was washed (water) dried (anhydrous magnesium sulphate) and the solvent evaporated to give, after trituration with ether, 4-bromo-3-ethoxy-2-(N-methylsulphonylamino) benzoic acid (3.44 g) as a white solid, NMR (DMSO-D$_6$) 1.4(t,3H), 3.2(s,3H), 3.3(brs,1H), 4.05(q,2H), 7.6(q,2H).

By proceeding in a similar manner the following compounds were prepared from the appropriately substituted starting materials:

4-bromo-2-(N-methylsulphonylamino)-3-methoxybenzoic acid, m.p. 181–188° C.;

4-fluoro-2-(N-methylsulphonylamino)benzoic acid (employing copper (I) chloride in place of copper (I) bromide);

4-bromo-2-(N-methylsulphonylamino)-3-(2,2,2-trifluoroethoxy)benzoic acid as a white solid, m.p. 191–193° C.;

3-chloro-4-fluoro-2-(N-methylsulphonylamino)benzoic acid, m.p. 157.5–161.5° C.;

3,4-difluoro-2-(N-methylsulphonylamino)benzoic acid, NMR (DMSO-D$_6$) 3.2(s,3H), 6.8(brs,1H), 7.4(m,1H), 7.75 (m,1H);

4-chloro-3-fluoro-2-(N-methylsulphonylamino)benzoic acid, m.p. 148–159.8° C. (containing some 4-chloro-3-fluorobenzoic acid);

3,4-dibromo-2-(N-methylsulphonylamino)benzoic acid, NMR (DMSO-D$_6$) 3.1(s,3H), 7.65(d,1H), 7.8(d,1H), 9.75(s, 1H);

3-chloro-2-(N-methylsulphonylamino)benzoic acid, NMR (DMSO-D$_6$) 3.05(s,3H), 6.8(s,1H), 7.35(t,1H), 7.7(m, 2H);

4-chloro-2-(N-methylsulphonylamino)benzoic acid, m.p. 188–192° C. from 2-bromo-4-chlorobenzoic acid, employing copper (I) bromide and methanesulphonamide and 3 equivalents of sodium hydride.

Also, by proceeding in a similar manner replacing methanesulphonamide with the appropriate N-alkylmethanesulphonamide the following compounds were prepared from the appropriately substituted starting materials:

4-iodo-2-(N-methyl-N-methylsulphonylamino)benzoic acid. m.p. 174–175° C. from 2-chloro-4-iodobenzoic acid;

2-(N-ethyl-N-methylsulphonylamino)benzoic acid, m.p. 116–118.5° C. (starting from 2-bromobenzoic acid).

Reference Example 14

Ethyl 2,4-dibromo-3-hydroxybenzoate (5.0 g) was added to a stirred suspension of potassium carbonate (106.4 g) in dry N,N-diethylformamide (DMF). A solution of iodomethane (25.7 g) in DMF was added over 18 minutes, and the resulting mixture was heated at 85° C. for 1.3 hours. The cooled mixture was poured onto water and extracted with ether. The extract was washed (brine solution), dried (anhydrous magnesium sulphate) and the solvent evaporated in vacuo to give ethyl 2,4-dibromo-3-ethoxybenzoate (52.08 g), NMR 1.4(t,3H), 1.5(t,3H), 4.1(q,2H), 4.4(q,2H), 7.35(d, 1H), 7.55(d,1H).

Reference Example 15

A mixture of concentrated sulphuric acid (128 ml) and acetic acid (192 ml) was added with stirring to 4-bromo-3-ethoxy-2-(N-ethyl-N-methylsulphonylamino)benzoic acid (8.8 g) at 85° C. for 100 minutes and left to stand at ambient temperature for 3 days. After pouring onto excess water, the mixture was made neutral by the careful addition of sodium hydroxide solution with cooling&g, extracted with ethyl acetate, dried (anhydrous magnesium sulphate) and the solvent evaporated to give 4-bromo-2-ethylamino-3-ethoxybenzoic acid (4.74 g) as a brown solid, m.p. 129–139° C.

By proceeding in a similar manner the following compounds were prepared from the appropriately substituted staring materials:

4-bromo-2-ethylamino-3-(2,2,2-trifluoroethoxy)benzoic acid, m.p. 179–180° C.;

4-bromo-2-ethylamino-3-methoxybenzoic acid, m.p. 129–135° C.

Reference Example 16

A solution of 4-bromo-3-ethoxy-2-(N-methylsulphonylamino)benzoic acid (10 g) in DMF was added to a stirred suspension of sodium hydride (3.55 g of a 60% oil dispersion) in DMF at 0° C. The mixture was slowly heated to 85° C., maintained at that temperature for 1 hour, cooled to 0° C. and ethyl iodide (27.7 g) added. After heating at 85° C. overnight. the cooled mixture was treated with ammonium chloride solution and extracted with ether. The extract was washed (brine solution), dried (anhydrous magnesium sulphate) and the solvent evaporated to give a brown gum which was purified by chromatography to yield ethyl 4-bromo-3-ethoxy-2-(N-ethyl-N-methylsulphonylamino)benzoate (3.4 g), m.p. 43–45° C.

By proceeding in a similar manner the following compounds were prepared from the appropriately substituted starting materials:

ethyl 4-bromo-2-(N-ethyl-N-methylsulphonylamino)-3-(2,2,2-trifluoroethoxy)benzoate as a white solid, m.p. 57–59° C.

ethyl 4-bromo-2-(N-ethyl-N-methylsulphonylamino)-3-methoxybenzoate, m.p. 69–72° C.;

ethyl 3-chloro-2-(N-ethyl-N-methylsulphonylamino)-4-fluorobenzoate, m.p. 76–79° C.;

ethyl 2-(N-ethyl-N-methylsulphonylamino)-3,4-difluorobenzoate, NMR 1.2(t,3H), 1.4(t,3H), 3.0(s,3H), 3.7(q,2H), 4.4(q,2H), 7.25(m,1H), 7.75(m,1H);

ethyl 4-chloro-2-(N-ethyl-N-methylsulphonylamino)-3-fluorobenzoate, NMR 1.2(t,3H), 1.4(t,3H), 3.0(s,3H), 3.7(q, 2H), 4.4(q,2H), 7.5(d,1H), 7.7(d,1H);

ethyl 3,4-dibromo-2(N-ethyl-N-methylsulphonylamino) benzoate, NMR 1.2(t,3H), 1.4(t,3H), 3.1(s,3H), 3.8(m,2H), 4.4(m,2H), 7.7(s,2H);

ethyl 3chloro-2-(N-ethyl-N-methylsulphonylamino) benzoate, NMR 1.15(t,3H), 1.3(t,3H), 3.0(s,3H), 3.75(m, 2H), 4.3(m,2H), 7.3(t,1H), 7.55(d,1H), 7.75(d,1H).

Reference Example 17

A mixture of ethyl 2,4-dibromo-3-hydroxybenzoate (5.0 g) and 1,3-dimethyl-3,4,5,6-tetrahydro-2(1H)-pyrimidinone (10 ml) was added to a stirred mixture of sodium hydride (60% oil dispersion, 0.617 g) and 1,3-dimethyl-3,4,5,6-tetrahydro-2(1H)-pyrimidinone under an inert atmosphere. The mixture was heated at 140° C. for 1 hour, cooled and 2,2,2-trifluoroethylpara-toluenesulphonate (4.71 g) was added. After heating at 140° C. for 18 hours, further 2,2,2-trifluoroethylpara-toluenesulphonate (4.71 g) was added, and the mixture was heated at 140° C. for 3 days. The cooled mixture was then poured onto water, extracted with ether, and the extract washed in turn with sodium hydroxide solution, water and brine. The extract was then dried (anhydrous magnesium sulphate) and the solvent evaporated to give ethyl 2,4-dibromo-3-trifluoethoxybenzoate (8.27 g), NMR 1.3(t,3H), 4.3(q,2H), 4.4(m,2H), 7.4(d,1H), 7.5(d, 1H).

Reference Example 18

A solution of methanethiol (4 ml) in dry DMF was added to a mixture of ethyl 3-chloro-2-(N-ethyl-N-methylsulphonylamino)-4-fluorobenzoate (7.4 g) and anhydrous potassium carbonate (4.71 g) in DMF at 40° C. The mixture was maintained at −10° C. for 1 hour, then warmed to ambient temperature over 2.5 hours. Water was added and the mixture extracted with ether, washed with brine solution then water, dried (anhydrous magnesium sulphate) and the solvent evaporated to give ethyl 3-chloro-2-(N-ethyl-N-methylsulphonylamino)-4-(methylthio)benzoate (8.3 g) as a white powder, m.p. 109–110.5° C.

By proceeding in a similar manner ethyl 2-(N-ethyl-N-methylsulphonylamino)-3-fluoro-(methylthio)benzoate was prepared, m.p. 70.5–73.5° C.

Reference Example 19 n-Butyl lithium (25M solution, 76 ml) was added to a stirred solution of diisopropylamine (28 ml) in dry tetrahydrofuran (THF) at −75° C., and maintained at −30° C. for a further 1 hour, to produce lithium diisopropylamide (LDA). After re-cooling to −75° C., a solution of 3 -chloro-4-fluorobenzoic acid (14.4 g) in dry THF was added over 1 hour, and stirring was continued overnight at −75° C. A solution of 1,2-dibromotetrachloroethane (42.77 g) in dry THF was then added over 20 minutes, stirring was continued for 2 hours at −70° C. then at room temperature for 4 hours. Water was added, the organic and aqueous phases were separated and the aqueous phase was washed with ether, then acidified with hydrochloric acid solution and extracted with dichloromethane. The dichloromethane extract was dried (anhydrous magnesium sulphate) and the solvent evaporated to give 2-bromo-3-chloro-4-fluorobenzoic acid (19.54 g) as a beige solid, NMR (DMSO-D$_6$) 7.55(t,1H), 7.75(dd,1H), 13.8(brs,1H).

By proceeding in a similar manner 2,3,4-tribromobenzoic acid was prepared, NMR (DMSO-D$_6$) 7.5(d,1H), 7.9(d,1H), 13.75(brs,1H).

Also, by proceeding in a similar manner but employing n-butyl lithium in place of LDA the following compounds were prepared:

2-bromo-3,4-difluorobenzoic acid, m.p. 162–170° C., 2-bromo-3-fluorobenzoic acid, NMR (DMSO-D$_6$) 7.55 (dd,1H), 7.8(dd,1H).

Reference Example 20

3,4-Dichloroanthranilic acid (61.8 g) was stirred in THF at −15° C., and triethylamine was added. Methyl chloroformate (36.9 g) was then added at −15° C. and the mixture stirred for 45 minutes. Water was then added, followed by concentrated hydrochloric acid solution until pH 1 was achieved, and the solution was stirred overnight. Excess water was added and the mixture was extracted with ethyl acetate. The extract was washed with water, dried (anhydrous magnesium sulphate) and the solvent evaporated The resulting solid was recrystallised from a solution of toluene and cyclohexane to give 3,4-dichloro-2-(methoxycarbonylamino)benzoic acid (65.1 g) as a fawn solid, m.p. 155–156° C.

Reference Example 21

Potassium carbonate (1.25 g) was added to a stirred solution of methyl 4-chloro-2-(N-methylsulphonylamino) benzoate (7.5 g) in acetone. The mixture was stirred for 15 minutes and methyl iodide (8.0 g) was added. The resultant mixture was stirred at room temperature for 1 hour and left to stand overnight The mixture was evaporated to dryness and the residue was dissolved in ethyl acetate and washed with sodium hydroxide solution (2M) and water, dried (anhydrous magnesium sulphate) and filtered. The filtrate was evaporated to dryness to give methyl 4-chloro-2-(N-methyl-N-methylsulphonylamino)benzoate (4.9 g) as a white solid, m.p. 73–75° C.

By proceeding in a similar manner the following compounds were prepared from the appropriately substituted starting materials:

ethyl 4-chloro-2-(N-ethyl-N-methylsulphonylamino) benzoate, NMR 1.1(t,3H) 135(t,3H) 2.9(s,3H) 3.65(q,2H) 4.3(q,2H) 7.3(d,1H) 7.35(s,1H) 7.8(d,1H);

methyl 3,4-dichloro-2-(N-methyl-N-methylsulphonylamino)benzoate, NMR 2.95(s,3H), 3.28(s, 3H), 3.89(s,3H), 7.5(d,1H), 7.71(d,1H);

methyl 2-(N-methyl-N-methylsulphonylamino)-4-trifluoromethylbenzoate, NMR 2.95(s,3H), 3.3(s,3H), 3.95 (s,3H), 7.25(m,2H), 8.0(d,1H);

methyl 4-dichloro-2-(N-isobutyl-N-methylsulphonylamino)benzoate, m.p. 89–90° C., employing isobutyl iodide instead of methyl iodide.

Referee Example 22

A solution of methanesulphonyl chloride (6.3 g) in dichloromethane was added to a stirred, cooled (0–5° C.) solution of methyl 2-amino chlorobenzoate (9.5 g) in dichloromethane. Triethylamine (7.1 g) was then added and the mixture was stirred at 0–5° C. for 10 minutes and then at room temperature for 0.5 hours. The mixture was diluted with 2N hydrochloric acid. The organic phase was separated, washed with water, dried and evaporated. The crude product was purified by column chromatography to yield methyl 4-chloro-2-(N-methylsulphonylamino)benzoate as a white solid, (3.6 g) m.p. 125.5–128.1° C.

Reference Example 23

A mixture of 2-amino-4-methylbenzoic acid (15.0 g) and concentrated sulphuric acid (20 ml) was heated under reflux with methanol for 18 hours. After removal of the solvent the residue was dissolved in dichloromethane, basified with sodium carbonate solution and the organic phase was washed with water, dried (anhydrous magnesium sulphate) and the solvent evaporated to give methyl 2-amino-4-methylbenzoate, m.p. 41–43° C.

By proceeding in a similar manner the following compounds were prepared from the appropriately substituted starting materials:

methyl 3,4-dichloro-2-(N-methyl-N-methylsulphonylamino)benzoate, NMR 2.95(s,3H), 3.28(s, 3H), 3.89(s,3H), 7.5(d,1H), 7.71(d,1H);

methyl 2-amino-4-trifluoromethylbenzoate m.p. 60–62° C.;

methyl 2-amino-3,4-difluorobenzoate.

Reference Example 24

An aqueous solution of sodium hydroxide (11.0 g) was added to a solution of a mixture of methyl 4-methyl-2-[N, N-bis(methylsulphonyl)amino]benzoate and methyl 4-methyl-2-(N-methylsulphonylamino)benzoate (2326 g) in methanol and the resulting suspension was heated at reflux for 1 hour. It was cooled and the methanol was removed by evaporation. The aqueous solution was acidified and the resultant solid was filtered off to give 4-methyl-2-(N-methylsulphonylamino)benzoic acid (16.42 g) as a cream solid, m.p. 202–205° C.

By proceeding in a similar manner the following compounds were prepared from the appropriately substituted starting materials:

4-bromo-2-(N-methylsulphonylamino)benzoic acid m.p. 178–186° C.;

2-(N-methylsulphonylamino)-4-trifluoromethylbenzoic acid.

Reference Example 25

Methanesulphonyl chloride (12.2 ml) was added to a stirred, cooled solution of methyl 2-aminomethylbenzoate (103 g) and triethylamine (193 ml) in dichloromethane while maintaining the temperature below 0° C. The mixture was stirred at room temperature for 4 hours. Hydrochloric acid solution (2M) was added and the layers were separated. The organic layer was washed with water, dried (magnesium sulphate) and filtered. The filtrate was evaporated to dryness to give a mixture of methyl 4-methyl-2-[N,N-bis (methylsulphonyl)amino]benzoate and methyl 4-methyl-2-(N-methylsulphonylamino)benzoate (18.26 g) as a yellow solid which was not further purified.

By proceeding in a similar manner the following compounds were prepared from the appropriately substituted starting materials:

methyl 2-[N,N-bis(methylsulphonyl)amino]-4-trifluoromethylbenzoate m.p. 159–163° C.;

methyl 4-bromo-2-[N,N-bis(methylsulphonyl)amino] benzoate, m.p. 221–225° C.;

methyl 3,4-difluoro-2-[N,N-bis(methylsulphonyl)amino] benzoate as a solid, NMR 3.42(s,6H), 3.87(s,3H), 73(q,1H), 7.79(m,1H);

methyl 2-[N,N-bis(methylsulphonyl)amino]-4-methylsulphonyl benzoate m.p. 207.4–211.2° C.;

methyl 2-(N-methylsulphonylamino)-4-trifluoromethoxybenzoate and methyl 2-[N,N-bis (methylsulphonyl)amino]-4trifluoromethoxybenzoate.

Reference Example 26

A mixture of ethyl 2-(N-ethyl-N-methylsulphonylamino)-4-methylsulphonylbenzoate (1.4 g) and lithium hydroxide monohydrate (1.37 g) in aqueous ethanol (50%) was stirred at room temperature for 19 hours. The mixture was then acidified with conc. hydrochloric acid and extracted with ethyl acetate. The combined organic extracts were dried (magnesium sulphate), filtered and evaporated to yield 2-(N-ethyl-N-methylsulphonylamino)-4-methylsulphonylbenzoic acid as a brown solid (9.48 g), NMR (acetone-$d_6$); 1.15(t, 3H), 2.98(s,3H), 322(s,3H), 3.85(q,2H), 8.0–8.25(m,3H).

Reference Example 27

A suspension of methyl 2-[N,N-bis(methylsulphonyl) amino]-4-methylsulphonylbenzoate (22.9 g) and lithium hydroxide monohydrate (7.5 g) in aqueous methanol (50%) was stirred at room temperature for 18 hours. The resulting solution was acidified with concentrated hydrochloric acid and extracted with ethyl acetate. The combined organic extracts were dried (magnesium sulphate), filtered and evaporated to yield 2-methylsulphonylamino-4-methylsulphonylbenzoic acid as a beige solid, NMR (acetone $d_6$); 3.1(2s,6H), 7.57(dd,1H), 8.15(d,1H), 8.23(d, 1H).

By proceeding in a similar manner 3,4-difluoro-2-(N-methylsulphonylamino)benzoic add was prepared as a brown solid.

Reference Example 28

Concentrated hydrochloric acid (90 ml) was added to a stirred suspension of methyl 2-nitro-4-methylsulphonylbenzoate (25 g) in methanol at −5° C. (ice/salt bath). The cooling bath was then removed and iron dust (175 g) was added portionwise over a period of 20 minutes. The resulting exotherm was controlled using a cooling bath so that the temperature did not exceed 50° C. After 15 minutes of cooling, the bath was removed and the reaction mixture was allowed to reach room temperature. Stirring was continued for a further 3 hours. The mixture was poured onto ice and then neutralised with sodium carbonate. Dichloromethane was added and the suspension was filtered. The filtrate was extracted with further dichloromethane and the combined organic extracts were dried (magnesium sulphate), filtered and evaporated to yield a crude product which was purified by recrystallisation from ethyl acetate/hexane to give methyl 2-amino-4methylsulphonylbenzoate (45 g) as yellow needles, m.p. 98.3–98.5° C.

Reference Example 29

A mixture of methyl 2-amino-3,4-dichlorobenzoate (2.2 g) and methanesulphonyl chloride (2.86 g) was stirred at 100° C. for 4 hours. A further quantity of methanesulphonyl chloride (2.86 g) was added and the mixture was stirred at 100° C. overnight. The mixture was poured into water then extracted with ethyl acetate. The combined organic extracts were washed with water, dried (magnesium sulphate) and evaporated to yield a brown oil which was crystallised from cyclohexane/ethyl acetate to yield methyl 3,4-dichloro-2-(methylsulphonylamino)benzoate as light brown crystals (1.4 g), m.p. 100–102° C.

Reference Example 30

6,7-Difluoroisatin (22.2 g) was added to a solution of sodium hydroxide (2N, 185 ml). Hydrogen peroxide (30%, 36 ml) was added at 40° C. or less over 20 minutes. After 1 hour the mixture was heated to 65° C. for 0.5 hours, cooled, poured onto water and acidified with concentrated hydrochloric acid. The resulting solid was filtered, washed with water and recrystallised from ethyl acetate/cyclohexane to give 2-amino-3,4-difluorobenzoic acid (11.3 g) as an orange solid, m.p. 207–208° C.

Reference Example 31

2,3-Difluoro-α-isonitrosoacetanilide (36.8 g) was added during 1 hour to a stirred solution of concentrated sulphuric acid and water at 65–75° C. After an additional 20 minutes at 80° C., the cooled mixture was poured onto excess ice-water. Extraction with ethyl acetate was followed by water washing, drying (magnesium sulphate) and evaporation to dryness to give a brown solid. Trituration with boiling cyclohexane gave after cooling, 6,7-difluoroisatin (22.2 g), m.p. 1645–167° C. as a brown solid.

Reference Example 32

Chloral hydrate (38.9 g) was added to a stirred solution of sodium sulphate (219 g) in water. A solution of 2,3-difluoroaniline (25 g) in a mixture of concentrated hydrochloric acid (19.4 ml) and water (1 17 ml) was added. A solution of hydroxylamine hydrochloride (41.35 g) in water was then added over 35 minutes and the mixture stirred for 1 hour at 95–100° C. After cooling the solid was filtered, washed with water, then with petroleum ether and dried in a desiccator to furnish 2,3-difluoro-α-isonitrosoacetanilide (36.8 g), m.p. 124.5–125° C.

Reference Example 33

A solution of sodium hydroxide (2.38 g) in water was added to a mixture of methyl 2-(N-methylsulphonylamino)-4trifluoromethoxybenzoate and methyl 2-[N,N-bis (methylsulphonyl)amino]-4trifluoromethoxybenzoate (8.26 g) in methanol at 15–20° C. After an additional 15 minutes the solid was filtered, dissolved in ethyl acetate, dried (magnesium sulphate) and evaporated in vacuo to give methyl 2-(N-methylsulphonylamino)-4trifluoromethoxybenzoate as a brown solid (4.15 g) after trituration with hexane, NMR 3.0(s,3H), 3.9(s,3H), 6.9(m, 1H), 7.55(m,1H), 8.05(d,1H), 10.5(brs,1H).

Reference Example 34

By following the procedure described in Example 1 above the following compounds were prepared from the appropriately substituted starting materials:

4-[4-bromo-3-ethoxy-2-(N-methyl-N-methylsulphonylamino)benzoyl]-5-cyclopropylisoxazole, m.p. 97–99° C.;

4-[4-chloro-2-(N-ethyl-N-methylsulphonylamino)benzoyl]-5-cyclopropylisoxazole, m.p. 114–115.8° C., 5-cyclopropyl-4-[4-methyl-2-(N-methyl-N-methylsulphonylamino)benzoyl]isoxazole, m.p. 120–122° C.;

4-[4-chloro-2-(N-propyl-N-methylsulphonylamino)
benzoyl]-5-cyclopropylisoxazole, m.p. 127–128° C.;
5-cyclopropyl-4-[2-(N-ethyl-N-methylsulphonylamino)-4-
methylsulphonylbenzoyl]isoxazole, m.p. 171–172° C.;
4-[3,4-dichloro-2-(N-methylsulphonylamino)benzoyl]-5-
cyclopropylisoxazole, m.p. 153–154° C.;
4-[4-bromo-2-(N-methyl-N-methylsulphonylamino)
benzoyl]-5-cyclopropylisoxazole, m.p. 128–130° C.;
4-[3,4-difluoro-2-(N-methyl-N-methylsulphonylamino)
benzoyl]-5-cyclopropylisoxazole, m.p. 134–136° C.;
4-[4-iodo-2-(N-methyl-N-methylsulphonylamino)benzoyl]-
5-cyclopropylisoxazole, m.p. 128–129° C.; and
4-[2-(N-isobutyl-N-methylsulphonylamino)-4-
chlorobenzoyl]-5-cyclopropylisoxazole, m.p. 118–118.5°
C.

Reference Example 35

By following the procedure described in Example 2 above the following compounds were prepared from the appropriately substituted starting materials:

5-cyclopropyl-4-[2-(N-ethyl-N-methylsulphonylamino)-
4-fluorobenzoyl]isoxazole, NMR 1.25(t,3H), 1.35(m,2H),
2.6(m1H), 3.0(s,3H), 3.7(q,2H), 7.2(m,2H), 7.5(t,1H), 8.2
(s,1H).

5cyclopropyl-4-[2-(N-ethyl-N-methylsulphonylamino)-
4-trifluoromethylbenzoyl]isoxazole, NMR 1.0(m,5H), 1.1
(m,2H), 2.5(m,1H), 2.7(s,3H), 3.5(q,2H), 7.4(d,1H), 7.5(m,
2H), 8.0(s,1H). 4-[4-chloro-2-(N-methyl-N-
methylsulphonylamino)benzoyl]-5-cyclopropyl-isoxazole,
m.p. 128.3–130.8° C.

5-cyclopropyl-4-[f2-(N-methyl-N-
methylsulphonylamino)-4 trifluoromethylbenzoyl]
isoxazole, NMR 1.2–15(m,4H), 2.65(m,1H), 2.95(s,3H),
3.3(s,3H), 7.6(dd,1H), 7.75(m,2H), 8.2(s,1H).

5-cyclopropyl-4-[2-(N-methyl-N-
methylsulphonylamino)-4-trifluoromethoxybenzoyl]
isoxazole, NMR 1.15(m,2H), 1.25(m,2H), 2.6(m,1H), 2.9(s,
3H), 3.2(s,3H), 7.2(m,2H), 7.5(d,1H), 8.1(s,1H).

5-cyclopropyl-4-[2-(N-ethyl-N-methylsulphonylamino)
benzoyl]isoxazole, m.p. 116–117.5° C.

4-[3-chloro-2-(N-ethyl-N-methylsulphonylamino)-4-
(methylthio)benzoyl]-5-cyclopropyl-isoxazole,
m.p.101–102° C.

5-cyclopropyl-4-[2-(N-ethyl-N-methylsulphonylamino)-
3,4-difluorobenzoyl]isoxazole, NMR 1.2(m,5H), 1.3(m,2H),
2.6(m,1H), 2.95(s,3H), 3.7(m,2H), 7.2(m,2H), 8.1(s,1H).

5-cyclopropyl-4-[2-(N-ethyl-N-methylsulphonylamino)-
3-fluoro-4-(methylthio)benzoyl]isoxazole, m.p.
118.5–120.5° C.

4-[4-chloro-2-(N-ethyl-N-methylsulphonylamino)-3-
fluorobenzoyl]-5-cyclopropylisoxazole, m.p. 126–128.5° C.

4-[3,4-dibromo-2-(N-ethyl-N-methylsulphonylamino)
benzoyl]-5-cyclopropylisoxazole, m.p. 169.5–171° C.

4-[3-chloro-2-(N-ethyl-N-methylsulphonylamino)
benzoyl]-5-cyclopropylisoxazole, m.p. 140–142° C.

According to a feature of the present invention, there is provided a method for controlling the growth of weeds (i.e. undesired vegetation) at a locus which comprises applying to the locus a herbicidally effective amount of at least one isoxazole derivative of formula (I) or an agriculturally acceptable salt thereof. For this purpose, the isoxazole derivatives are normally used in the form of herbicidal compositions (i.e. in association with compatible diluents or carriers and/or surface active agents suitable for use in herbicidal compositions), for example as hereinafter described. The compounds of formula (I) show herbicidal activity against dicotyledonous (i.e. broad-leafed) and monocotyledonous (i.e. grass) weeds by pre- and/or post-emergence application. By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, *Abutilon theophrasti, Amaranthus retroflexus, Bidens pilosa, Chenopodium album, Galium aparine,* Ipomoea spp. e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crus-galli, Sorghum bicolor, Eleusine indica* and Setaria spp, e.g. *Setaria faberii* or *Setaria viridis,* and sedges, for example, Cyperus esculentus.

The amounts of compounds of formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops,. for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and allow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application in a directional or non-directional fashion (e.g. by directional or non-directional spraying) at application rates between 1.0 kg and 20.0 kg, and preferably between 5.0 and 10.0 kg, of active material per hectare are particularly suitable for this purpose. When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

According to a further feature of the present invention, there are provided compositions suitable for herbicidal use comprising one or more of the isoxazole derivatives of formula (I) or agriculturally acceptable salts thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent. for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of formula (I), from 2 to 10% of surface-active agent, from 0.1 to 5% of thickener and from 15 to 87.9% of water, wettable powders which comprise from 10 to 90% of one or more compounds of formula (I), from 2 to 10% of surface-active agent and from 8 to 88% of solid diluent or carrier, water soluble or water dispersible powders which comprise from 10 to 90% of one or more compounds of formula (I), from 2 to 40% of sodium carbonate and from 0 to 88% of solid diluent; liquid water soluble concentrates which comprise from 5 to 50%, e.g. 10 to 30%, of one or more compounds of formula (I), from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%, e.g. 2 to 10% of one or more compounds of formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine[2-chloro-4-ethylamino-6-isopropylamino-1,3,5-triazine], bromoxynil[3,5-dibromo-4-hydroxybenzonitrile], chlortoluron[N'-(3chloro-4-methylphenyl)-N,N-dimethylurea], cyanazine[2-chloro-4-(1cyano-1-methylethylamino)-6-ethylamino-1,3,5-triazine], 2,4-D[2,4-dichlorophenoxy-acetic acid], dicamba[3,6-dichloro-2-methoxybenzoic acid], difenzoquat[1,2-dimethyl-3,5-diphenyl-pyrazolium salts], flampropmethyl[methyl N-2-(N-benzoyl-3-chloro-4fluoroanilino)-propionate], fluometuron[N'-(3-trifluoromethylphenyl)-N,N-(dimethylurea], isoproturon[N'-(4-isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chlorophenoxy)-3,3- dimethyl-1-(1,2,triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one isoxazole derivative of formula (I) or an agriculturally acceptable salt thereof or, as is preferred, a herbicidal composition as hereinbefore described, and preferably a herbicidal concentrate which must be diluted before use, comprising at least one isoxazole derivative of formula (I) or an agriculturally acceptable salt thereof within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the isoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

Example C1

A soluble concentrate is formed from:

| | |
|---|---|
| Active ingredient (compound 1) | 20% w/v |
| Potassium hydroxide Solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 is obtained then making up to volume with water.

Similar soluble concentrates may be prepared as described above by replacing the isoxazole (compound 1) with other compounds of formula (I).

Example C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula (I).

Example C3
A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula (I).

The compounds of the invention have been used in herbicidal applications according to the following procedures.

Method of use of Herbicidal Compounds a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2 |
| 2) Grass weeds | |
| Alopecurus myosuroides | 15 |
| Avena fatua | 10 |
| Echinochloa crus-galli | 15 |
| Setaria viridis | 20 |
| 3) Sedges | |
| Cyperus esculentus | 3 |
| Crop | |
| 1) Broad leafed | |
| Cotton | 3 |
| Soya | 3 |
| 2) Grass | |
| Maize | 2 |
| Rice | 6 |
| Wheat | 6 |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| | Number of plants per pot | Growth stage |
|---|---|---|
| Weed Species | | |
| 1) Broad leafed weeds | | |
| Abutilon theophrasti | 3 | 1–2 leaves |
| Amaranthus retroflexus | 4 | 1–2 leaves |
| Galium aparine | 3 | $1^{st}$ whorl |
| Ipomoea purpurea | 3 | 1–2 leaves |
| Sinapis arvensis | 4 | 2 leaves |
| Xanthium strumarium | 1 | 2–3 leaves |
| 2) Grass weeds | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Cyperus esculentus | 3 | 3 leaves. |
| Crops | | |
| 1) Broad leafed | | |
| Cotton | 2 | 1 leaf |
| Soya | 2 | 2 leaves. |
| 2) Grass | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

The compounds of the invention, used at 4 kg/ha or less, have shown an excellent level of herbicidal activity together with crop tolerance on the weeds used in the foregoing experiments.

When applied pre- or post-emergence at 1000 g/ha or less compounds 1 to 50 gave at least 90% reduction in growth of one or more of the weed species.

What is claimed is:

1. A compound having the formula:

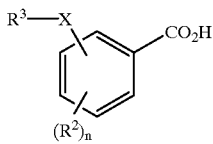

(XVI)

wherein:

R² represents a halogen atom or a group selected from trifluoromethyl, methyl, $C_{1-2}$ haloalkoxy and $S(O)_p$ $CH_3$ wherein p is zero, one or two;

X represents —$NR^{8'}$ wherein $R^{8'}$ represents alkyl or alkenyl having up to four carbon atoms optionally substituted by one or more halogen atoms;

n represents one or two; and

R³ represents —C(Z)=Y wherein Y is oxygen, Z is $R^{63}$ or —$OR^{63}$, and $R^{63}$ represents alkyl having up to four carbon atoms.

2. A compound according to claim 1 in which the 2-position of the benzene ring is substituted.

3. A compound according to claim 1 in which the 5- and 6-positions of the benzene ring are unsubstituted.

4. A compound according to claim 2 in which the 5- and 6-positions of the benzene ring are unsubstituted.

5. A compound according to claim 1 in which R² represents halogen and $R^{8'}$ represents an alkyl having up to four carbon atoms.

6. A compound having the formula:

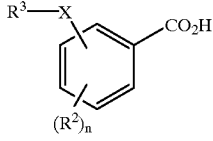

(XVI)

wherein:

R² represents a halogen atom or a group selected from trifluoromethyl, methyl, $C_{1-2}$ haloalkoxy and $S(O)_p$ $CH_3$ wherein p is zero, one or two;

X represents —$NR^{8'}$ wherein $R^{8'}$ represents alkyl or alkenyl having up to four carbon atoms optionally substituted by one or more halogen atoms;

n represents one or two; and

R³ represents —C(Z)=Y wherein Y is oxygen, Z is $R^{63}$ or —$OR^{63}$, and $R^{63}$ represents alkyl having up to four carbon atoms optionally substituted by one or more halogen atoms; and wherein the compound is selected from the group consisting of:

3,4-dichloro-2-(N-methyl-N-ethoxycarbonylamino)benzoic acid;

3,4-dichloro-2-(N-ethyl-N-methoxycarbonylamino)benzoic acid;

3,4-dichloro-2-(N-methyl-N-methoxycarbonylamino) benzoic acid;

3,4-dichloro-2-(N-methyl-N-isopropyloxycarbonylamino) benzoic acid;

3,4-dichloro-2-(N-propyl-N-methoxycarbonylamino) benzoic acid;

3,4-dichloro-2-(N-isopropyl-N-methoxycarbonylamino) benzoic acid;

3,4-dichloro-2-(N-allyl-N-methoxycarbonylamino)benzoic acid;

3,4-dichloro-2-(N-ethyl-N-propyloxycarbonylamino) benzoic acid;

3,4-dichloro-2-(N-ethyl-N-ethoxycarbonylamino)benzoic acid;

3,4-dichloro-2-(N-ethyl-N-isopropylcarbonylamino) benzoic acid;

3,4-dichloro-2-(N-ethyl-N-n-butyloxycarbonylamino) benzoic acid; and 4-bromo-2-(N-ethyl-N-methoxycarbonylamino)-3-(2,2,2-trifluoroethoxy)benzoic acid.

* * * * *